US007820439B2

(12) United States Patent
Alam et al.

(10) Patent No.: US 7,820,439 B2
(45) Date of Patent: Oct. 26, 2010

(54) IN VITRO GENERATION OF GABAERGIC NEURONS FROM PLURIPOTENT STEM CELLS

(75) Inventors: Khan Firdos Alam, Navi (IN); Totey Satish Mahadeorao, Wadala (IN)

(73) Assignee: Reliance Life Sciences PVT Ltd., Sewri, Mumbai, Maharashtra (IN)

(*) Notice: Subject to any disclaimer, the term of this patent is extended or adjusted under 35 U.S.C. 154(b) by 969 days.

(21) Appl. No.: 10/930,675

(22) Filed: Aug. 31, 2004

(65) Prior Publication Data

US 2005/0095702 A1  May 5, 2005

Related U.S. Application Data

(60) Provisional application No. 60/557,895, filed on Mar. 31, 2004.

(30) Foreign Application Priority Data

Sep. 3, 2003  (IN) .................. 901/MUM/2003

(51) Int. Cl.
 *C12N 15/02* (2006.01)
(52) U.S. Cl. ...................... 435/377; 435/375
(58) Field of Classification Search ............... 435/375, 435/377
 See application file for complete search history.

(56) References Cited

U.S. PATENT DOCUMENTS

| | | |
|---|---|---|
| 5,453,357 A | 9/1995 | Hogan |
| 5,514,552 A | 5/1996 | Rosner et al. |
| 5,670,372 A | 9/1997 | Hogan |
| 5,690,296 A | 11/1997 | Biagiotti |
| 5,843,780 A | 12/1998 | Thomson |
| 5,914,268 A | 6/1999 | Keller et al. |
| 6,090,622 A | 7/2000 | Gearhart et al. |
| 6,200,806 B1 | 3/2001 | Thomson |
| 6,602,680 B2 | 8/2003 | Rubenstein et al. |
| 6,602,711 B1 | 8/2003 | Thomson et al. |
| 6,800,480 B1 | 10/2004 | Bodnar et al. |
| 2002/0009743 A1 | 1/2002 | Carpenter |
| 2002/0019046 A1 | 2/2002 | Carpenter et al. |
| 2002/0022268 A1 | 2/2002 | Xu et al. |
| 2002/0039724 A1 | 4/2002 | Carpenter |
| 2002/0151053 A1 | 10/2002 | Carpenter et al. |
| 2002/0168766 A1 | 11/2002 | Gold et al. |
| 2003/0017589 A1 | 1/2003 | Mandalam et al. |
| 2003/0036195 A1 | 2/2003 | Studer et al. |
| 2003/0068819 A1 | 4/2003 | Zhang et al. |
| 2003/0103949 A1 | 6/2003 | Carpenter et al. |
| 2003/0104616 A1 | 6/2003 | Parikh et al. |
| 2004/0014210 A1 | 1/2004 | Jessell et al. |
| 2004/0092012 A1 | 5/2004 | Okano et al. |
| 2005/0221479 A1 | 10/2005 | Nakayama et al. |
| 2006/0014280 A1 | 1/2006 | Condie et al. |

FOREIGN PATENT DOCUMENTS

| | | |
|---|---|---|
| WO | WO 98/30679 | 7/1998 |
| WO | WO 99/20741 | 4/1999 |
| WO | WO 01/51616 | 7/2001 |
| WO | WO 01/66697 | 9/2001 |
| WO | WO 01/83715 | 11/2001 |
| WO | WO 01/88104 | 11/2001 |
| WO | WO 02/086073 | 10/2002 |
| WO | WO 03/000868 | 1/2003 |
| WO | WO 03/020920 | 3/2003 |
| WO | WO 03/104444 | 12/2003 |
| WO | WO 2004/015077 | 2/2004 |

OTHER PUBLICATIONS

Chassande et al. (1995, Journal of Cell Science 108 : 3181-3188).*
Ponzoni et al. (1991, Cellular and Molecular Neurobiology, vol. 11, No. 4, pp. 397-413).*
Zulewski et al. 2001, Diabetes, vol. 50, pp. 521-533.*
Okabe et al. Development of Neuronal Precursor Cells and Functional Postmitotic Neurons From Embryonic Stem Cells In Vitro. Mechanisms Develop., 1996, vol. 59, pp. 89-102.*
Roy, N.S., et al., "In Vitro neurogenesis by progenitor cells isolated from the adult human hippocampus," Nature Medicine; 6(3):271-277, 2000.
Åkerud et al., "Neuroprotection through Delivery of Glial Cell Line-Derived Neurotrophic Factor by Neural Stem Cells in a Mouse Model of Parkinson's Disease." *J. Neurosci.* 21:8108-8118 (2001).
Bain et al, "Embryonic Stem Cells Express Neuronal Properties in Vitro." *Developmental Biology* 168:342-357 (1995).
Bain et al., "Expression of the Genes Coding for Glutamic Acid Decarboxylase in Pluripotent Cell Lines." *Molecular Brain Research* 17:23-30 (1993).
Bergman et al., "Physiological Aspects of Information Processing in the Basal Ganglia of Normal and Parkinsonian Primates." *TINS* 21:32-38 (1998).
Björklund et al., "Embryonic Stem Cells Develop Into Functional Dopaminergic Neurons After Transplantation in a Parkinson Rat Model." *PNAS* 99:2344-2349 (2002).
Björklund et al., "Reinnervation of the Denervated Striatum by Substantianigra Transplants: Functional Consequences as Revealed by Pharmacological and Sensorimotor Testing." *Brain Research* 199:307-333 (1980).
Brundin et al, "Intracerebral Grafting of Dopamine Neurons." *Annals of the N. Y. Acad. Sci.* 495:473-496 (1987).

(Continued)

*Primary Examiner*—Deborah Crouch
(74) *Attorney, Agent, or Firm*—Vinson & Elkins LLP

(57) ABSTRACT

The present disclosure is directed to improved methods for efficiently producing neuroprogenitor cells and differentiated neural cells such as GABAergic neurons from pluripotent stem cells, for example embryonic stem cells. Using the disclosed methods, cell populations containing a high proportion of GABAergic neurons have been isolated. The neuroprogenitor cells and terminally differentiated cells of the present disclosure can be generated in large quantities, and therefore may serve as an excellent source for cell replacement therapy in neurodegenerative disorders and neuronal diseases such as stroke, ischemia, epilepsy, and Huntington's disease.

29 Claims, 11 Drawing Sheets

OTHER PUBLICATIONS

Brüstle et al., "Chimeric Brains Generated by Intraventricular Transplantation of Fetal Human Brain Cells Into Embryonic Rats." *Nature Biotechnology* 16:1040-1044 (1998).

Brtüstle et al, "Embryonic Stem Cell-Derived Glial Precursors: A Source of Myelinating Transplants." *Science Magazine* 285:754-56 (1999).

Buehr et al., "Mesonephric Contribution to Testis Differentiation in the Fetal Mouse." *Development* 117:273-281 (1993).

Collier et al., "Cryopreservation of Fetal Rat and Non-Human Primate Mesencephalic Neurons: Viability in Culture and Neural Transplantation." *Progress in Brain Research* 78:631-636 (1988).

Collier et al., "Intracerebral Grafting and Culture of Cryopreserved Primate Dopamine Neurons." *Brain Research* 436:363-366 (1987).

Damjanov et al., "Retinoic Acid-Induced Differentiation of the Developmentally Pluripotent Human Germ Cell Tumor-Derived Cell Line, NCCIT." *Laboratory Investigation* 68:220-232 (1993).

Deacon et al., "Blastula-Stage Stem Cells Can Differentiate Into Dopaminergic and Serotonergic Neurons After Transplantation." *Experimental Neurology* 149:28-41 (1998).

Dunnett et al., "Behavioural Recovery Following Transplantation of Substantia Nigra in Rats Subjected to 6-OHDA Lesions of the Nigrostriatal Pathway .I. Unilateral Lesions." *Brain Research* 215:147-161 (1981).

Dunnett et al., "Intracerebral Grafting of Neuronal Cell Suspensions v. Behavioural Recovery in Rats with Bilateral 6-OHDA Lesions Following Implantation of Nigral Cell Suspensions." *Acta Physiol. Scan. Suppl.* 522:39-47 (1983).

Eder et al., "Short Communication $GABA_A$ and $GABA_B$ Receptors on Neocortical Neurons Are Differentially Distributed." *European Journal of Neuroscience* 13:1065-1069 (2001).

Eriksson et al., "Neurogenesis in the Adult Human Hippocampus." *Nature America, Inc.* 4:1313-1317 (1998).

Evans et al., "Establishment in Culture of Pluripotent Cells From Mouse Embryos." *Nature* 292:154-156 (1981).

Flax et al., "Engraftable Human Neural Stem Cells Respond to Developmental Cues, Replace Neurons, and Express Foreign Genes." *Nature Biotechnology* 16:1033-1039 (1998).

Freed et al., "Transplantation of Embryonic Dopamine Neurons for Severe Parkinson's Disease." *New England Journal of Medicine* 344:710-19 (2001).

Fricker et al., "Site-Specific Migration and Neuronal Differentiation of Human Neural Progenitor Cells After Transplantation in the Adult Rat Brain." *Journal of Neuroscience* 19:5990-6005 (1999).

Grisolía "CNS Stem Cell Transplantation: Clinical and Ethical Perspectives." *Brain Research Bulletin* 57:823-826 (2002).

Hancock et al., "Neuronal Differentiation of Cryopreserved Neural Progenitor Cells Derived from Mouse Embryonic Stem Cells." *Biochemical and Biophysical Research Communications* 271:418-421 (2000).

Henderson et al, "Neurotrophic Factors in Development and Plasticity of Spinal Neurons." *Restorative Neurology and Neuroscience* 5:15-28 (1993).

Hofer and Barde, "Brain-derived Neurotrophic Factor Prevents Neuronal Death in vivo." *Nature* 331:261-262 (1988).

Iannaccone et al., "Pluripotent Embryonic Stem Cells From The Rat Are Capable of Producing Chimeras." *Developmental Biology* 163:288-292 (1994).

Kawasaki et al., "Induction of Midbrain Dopaminergic Neurotechnique Neurons from ES Cells by Stromal Cell-Derived Inducing Activity." *Neuron* 28:31-40 (2000).

Kim et al., "Dopamine Neurons Derived from Embryonic Stem Cells Function in an Animal Model of Parkinson's Disease." *Nature* 418:50-56 (2002).

Kukekov et al., "Multipotent Stem/Progenitor Cells with Similar Properties Arise From Two Neurogenic Regions of Adult Human Brain." *Exper. Neurology* 156:333-344 (1999).

Lauder and Bloom, "Ontogeny of Monoamine Neurons in the Locus Coeruleus, Raphe Nuclei and Substantia Nigra of the Rat." *J. Comp. Neur.* 155:469-481 (1974).

Lee et al., "Efficient Generation of Midbrain and Hindbrain Neurons From Mouse Embryonic Stem Cells." *Nature Biotech.* 18:675-679 (2000).

Mary Ann Liebert, Inc., "National Institutes of Health Recombinant DNA Advisory Committee (RAC) Building 45/Natcher Conference Center, Conference Room D Bethesda, Maryland, Jun. 14-15, 2001; Meeting Agenda." *Human Gene Therapy* 12:15871598 (2001).

Lin et al., "GDNF: A Glial Cell Line-Derived Neurotrophic Factor for Midbrain Dopaminergic Neurons." *Science* 260:1130-32 (1993).

Lin et al., "Purification and Initial Characterization of Rat B49 Glial Cell Line-Derived Neurotrophic Factor." *Jour. of Neurochem.* 63:758-768 (1994).

Luo et al., "Subthalamic GAD Gene Therapy in a Parkinson's Disease Rat Model." *Science* 298:425-429 (2002).

Martin, "Isolation of a Pluripotent Cell Line From Early Mouse Embryos Cultured in Medium Conditioned by Teratocarcinoma Stem Cells." *Proc. Natl. Acad. Sci.* 78:7634-7638 (1981).

Matsui et al., "Derivation of Pluripotent Embryonic Stem Cells from Murine Primordial Germ Cells in Culture." *Cell* 70:841-847 (1992).

Nadaud et al., "Functional Recovery Following Transplantation of Ventral Mesencephalic Cells in Rat Subjected to 6-OHDA Lesions of the Mesolimbic Dopaminergic Neurons." *Brain Research* 304:137-141 (1984).

Nakao et al., "Overexpressing Cu/Zn Superoxide Dismutase Enhances Survival of Transplanted Neurons in a Rat Model of Parkinson's Disease." *Nature Medicine* 1:226-231 (1995).

Nishino, et al., "$GABA_A$ Receptor but Not Muscarinic Receptor Density Was Decreased in the Brain of Patients with Parkinson's Disease." *Japan. J. Pharmacol.*, 48:331-339 (1988).

Reubinoff et al., "Embryonic Stem Cell Lines From Human Blastocysts: Somatic Differentiation in vitro." *Nature Biotech.* 18:399-404 (2000).

Reubinoff et al., "Neural Progenitors From Human Embryonic Stem Cells." *Nature Biotechnology* 19:1134-1140 (2001).

Reynolds and Weiss, "Generation of Neurons and Astrocytes From Isolated Cells of the Adult Mammalian Central Nervous System." *Science* 255:1707-1710 (1992).

Rolletschek et al., "Differentiation of Embryonic Stem Cell-Derived Dopaminergic Neurons is Enhanced by Survival-Promoting Factors." *Mech. Dev.* 105:93-104 (2001).

Rosenthal, "Auto Transplants for Parkinson's Disease?" *Neuron* 20:169-172 (1998).

Seidl et al., "Differences Between GABA Levels in Alzheimer's Disease and Down Syndrome With Alzheimer-Line Neuropathology." *Naunyn-Schmiedeberg's Arch Pharmacol* 363:139-145 (2001).

Shamblott et al., "Derivation of Pluripotent Stem Cells From Cultured Human Primordial Germ Cells." *Proc. Natl. Acad. Sci.* 95:13726-13731 (1998).

Shihabuddin et al., "Adult Spinal Cord Stem Cells Generate Neurons After Transplantation in the Adult Dentate Gyrus." *Jour. of Neuroscience* 20:8727-8735 (2000).

Strömberg et al., "Glial Cell Line-Derived Neurotrophic Factor is Expressed in the Developing but Not Adult Striatum and Stimulates Developing Dopamine Neurons in vivo." *Experimental Neurology* 124:401-412 (1993).

Svendsen et al., "Long-Term Survival of Human Central Nervous System Progenitor Cells Transplanted into a Rat Model of Parkinson's Disease." *Experimental Neurology* 148:135-146 (1997).

Thomson et al., "Embryonic Stem Cell Lines Derived from Human Blastocysts." *Science* 282:1145-47 (1998).

Thomson et al., "Isolation of a Primate Embryonic Stem Cell Line." *Proc. Natl. Acad. Sci.* 92:7844-7848 (1995).

Thomson and Marshall, "Primate Embryonic Stem Cells." *Dev. Biology* 38:133-165 (1998).

Vescovi et al., "Isolation and Cloning of Multipotential Stem Cells from the Embryonic Human CNS and Establishment of Transplantable Human Neural Stem Cell Lines by Epigenetic Stimulation." *Exper. Neurology* 156:71-83 (1999).

Vescovi et al., "Isolation and Intracerebral Grafting of Nontransformed Multipotential Embryonic Human CNS Stem Cells." *Journal of Neurotrauma 16:689-693* (1999).

Westmoreland et al., "Neuronal Development of Embryonic Stem Cells: A Model of GABAergic Neuron Differentiation." *Biochemical and Biophysical Research Communications 284:674-680* (2001).

Williams et al., "Myeloid Leukaemia Inhibitory Factor Maintains the Developmental Potential of Embryonic Stem Cells." *Nature 336:684-687* (1988).

Winkler et al., "Transplantation in the Rat Model of Parkinson's Disease: Ectopic Versus Homotopic Graft Placement." *Progress in Brain Research 127:233-265*.

Yurek and Sladek, "Dopamine Cell Replacement: Parkinson's Disease." *Annu. Rev. Neurosci. 13:415-40* (1990).

Zhang et al., "In vitro Differentiation of Transplantable Neural Precursors From Human Embryonic Stem Cells." *Nature Biotech. 19:1129-1133* (2001).

\* cited by examiner

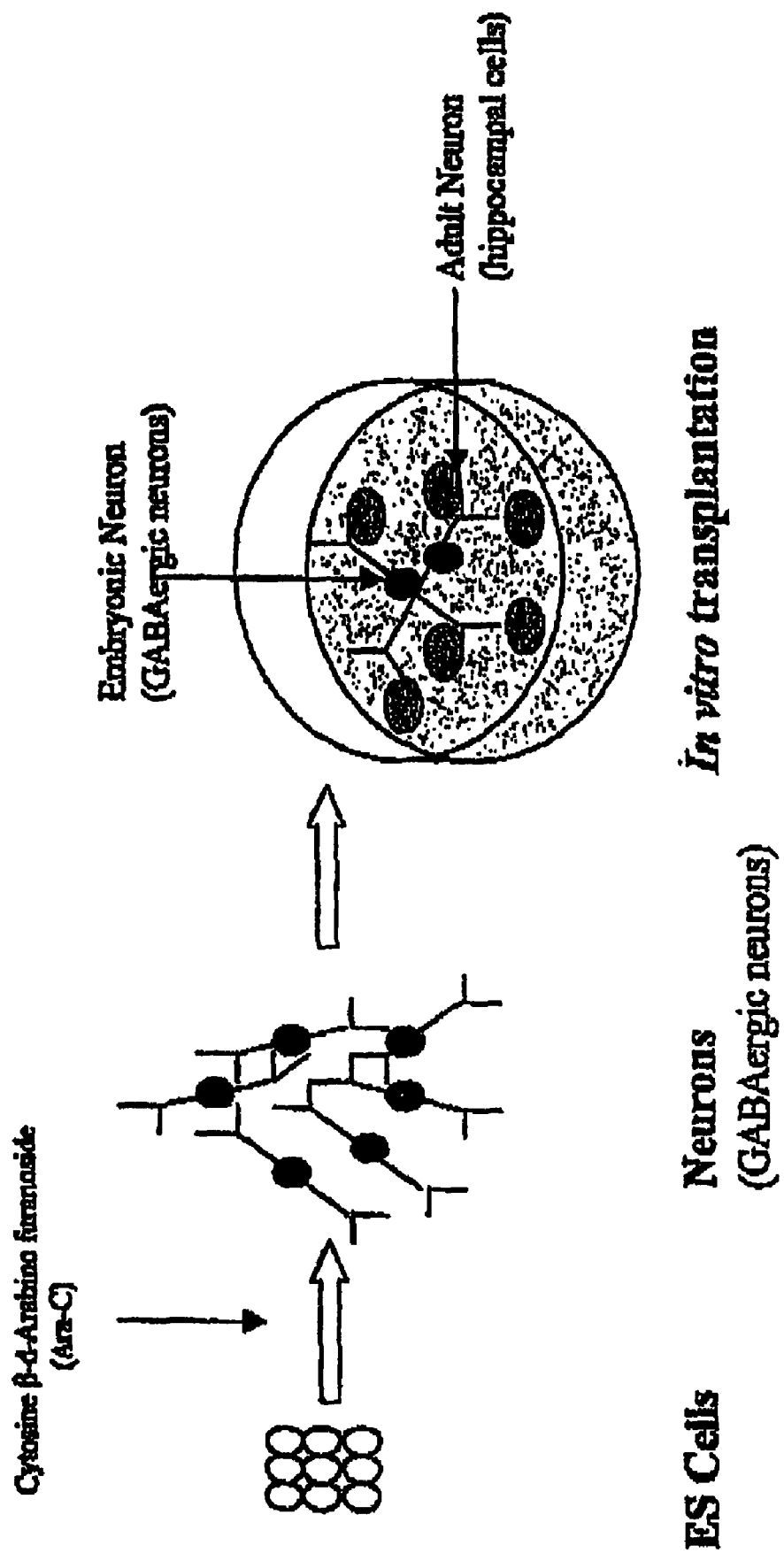

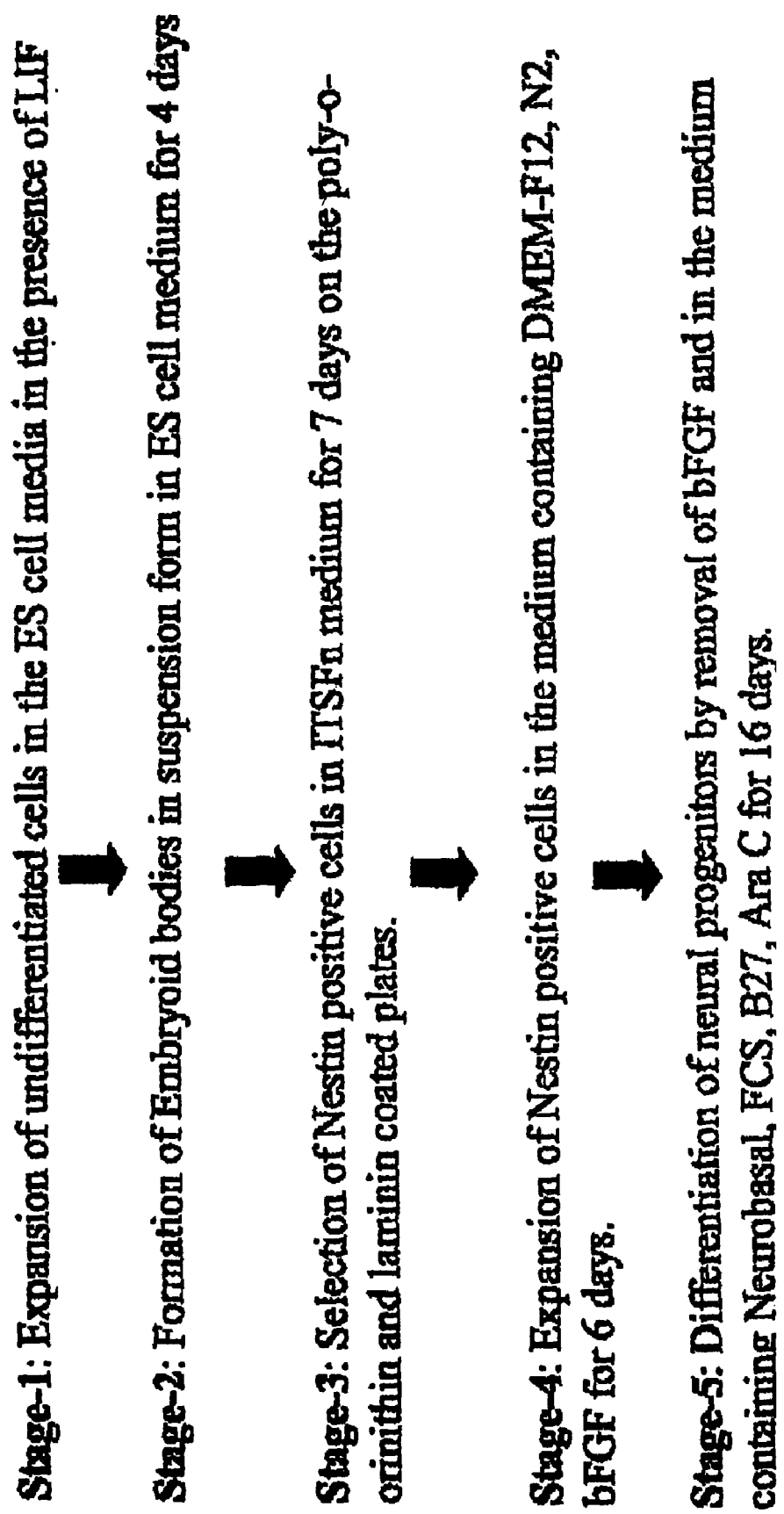

Figure-2

Development pathway

Stage-1: Expansion of undifferentiated cells in the ES cell media in the presence of LIF Stage-2: Formation of Embryoid bodies in suspension form in ES cell medium for 4 days Stage-3: Selection of Nestin positive cells in ITSFn medium for 7 days on the poly-o-ornithin and laminin coated plates.

Stage-4: Expansion of Nestin positive cells in the medium containing DMEM-F12, N2, bFGF for 6 days.

Stage-5: Differentiation of neural progenitors by removal of bFGF and in the medium containing Neurobasal, FCS, B27, Ara C for 16 days.

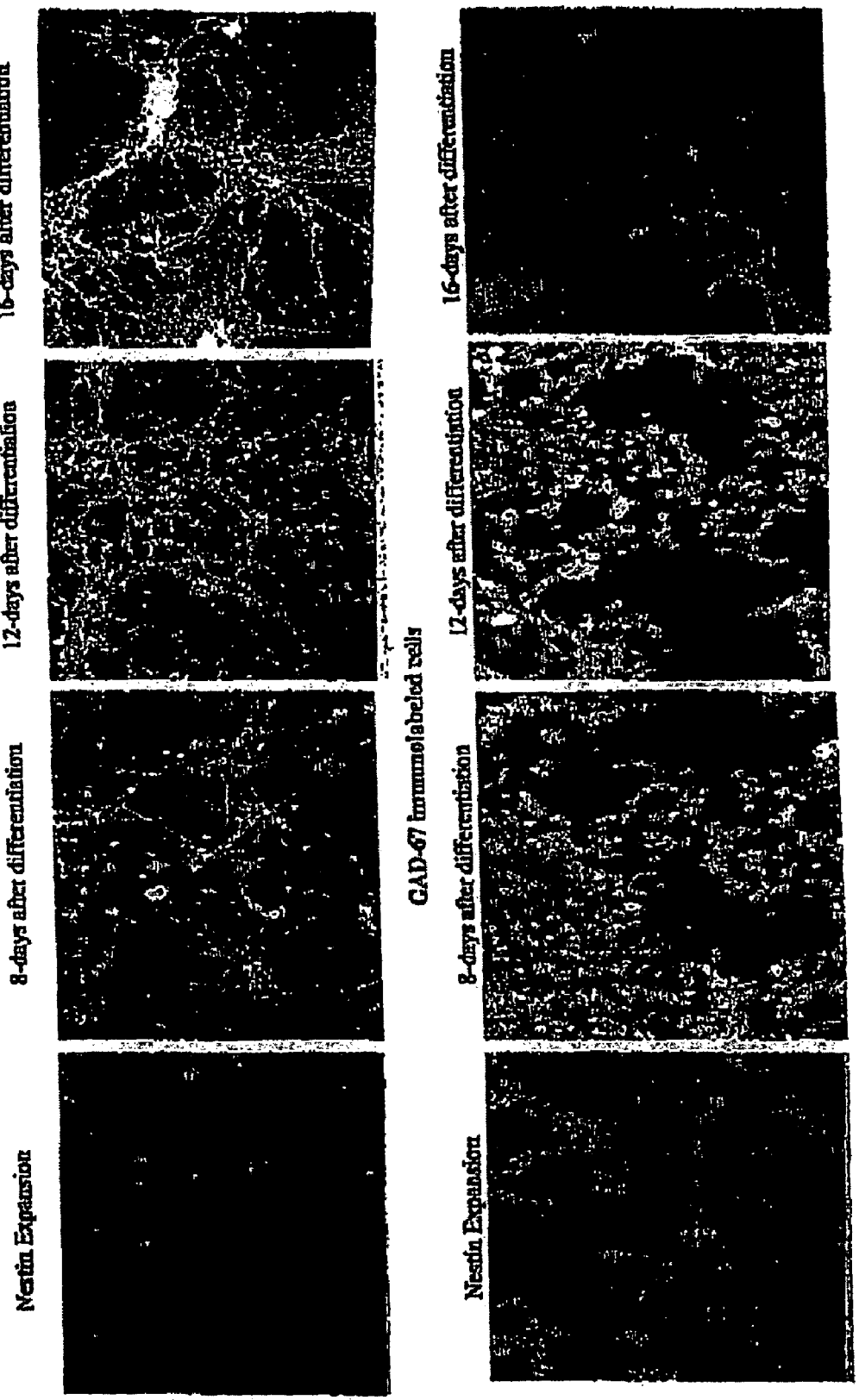

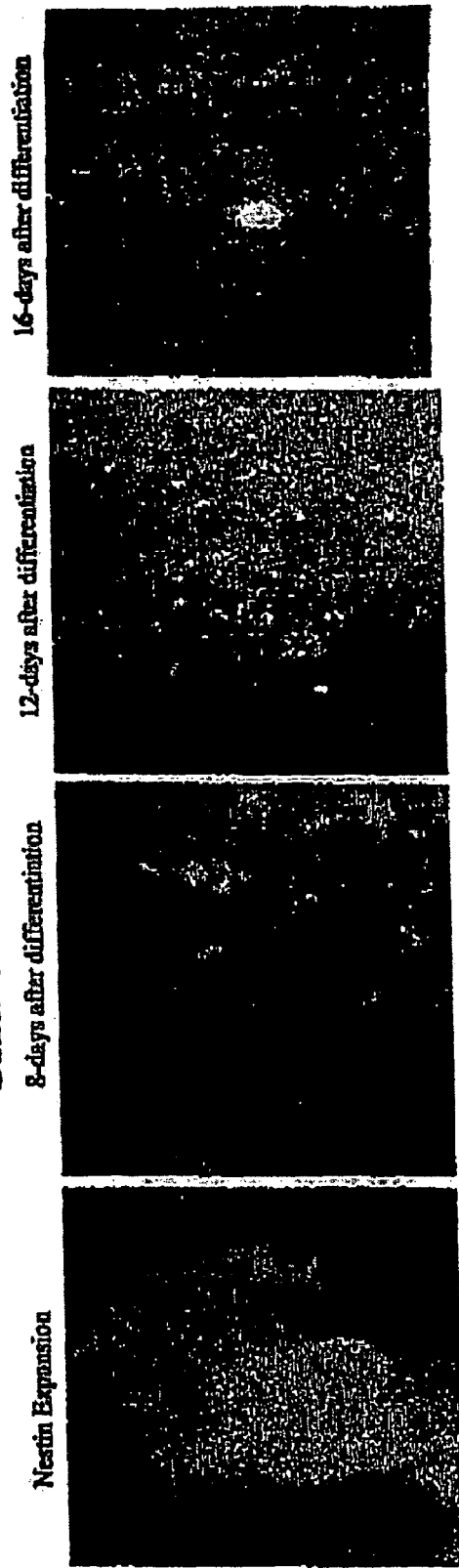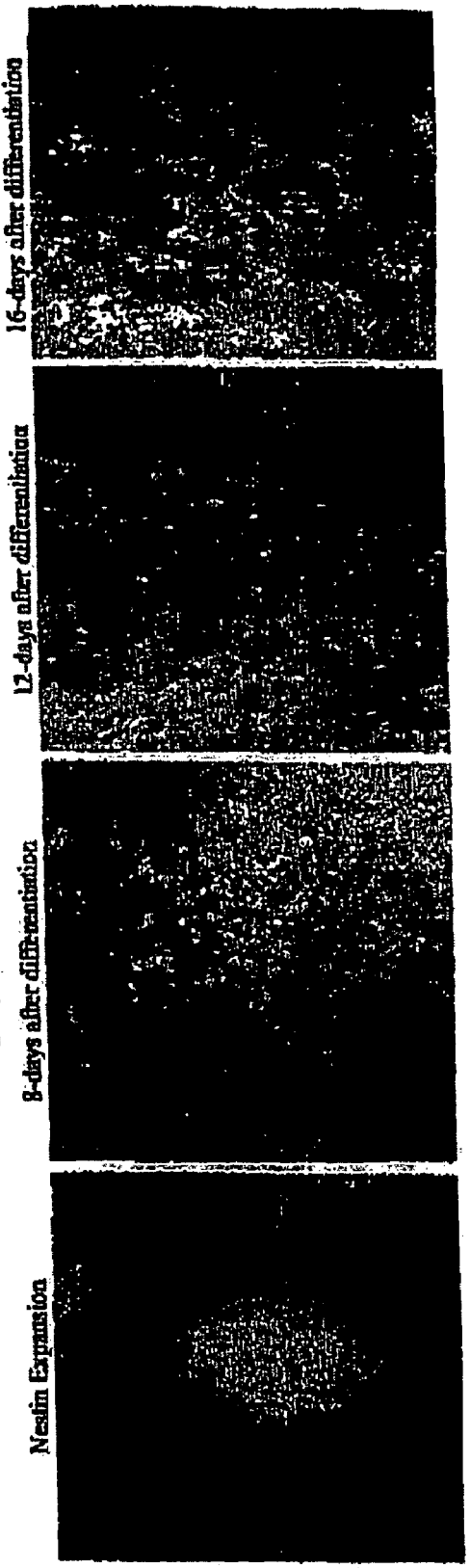
Figure-3b
GAT-1 immunolabeled cells
GAT-2 immunolabeled cells

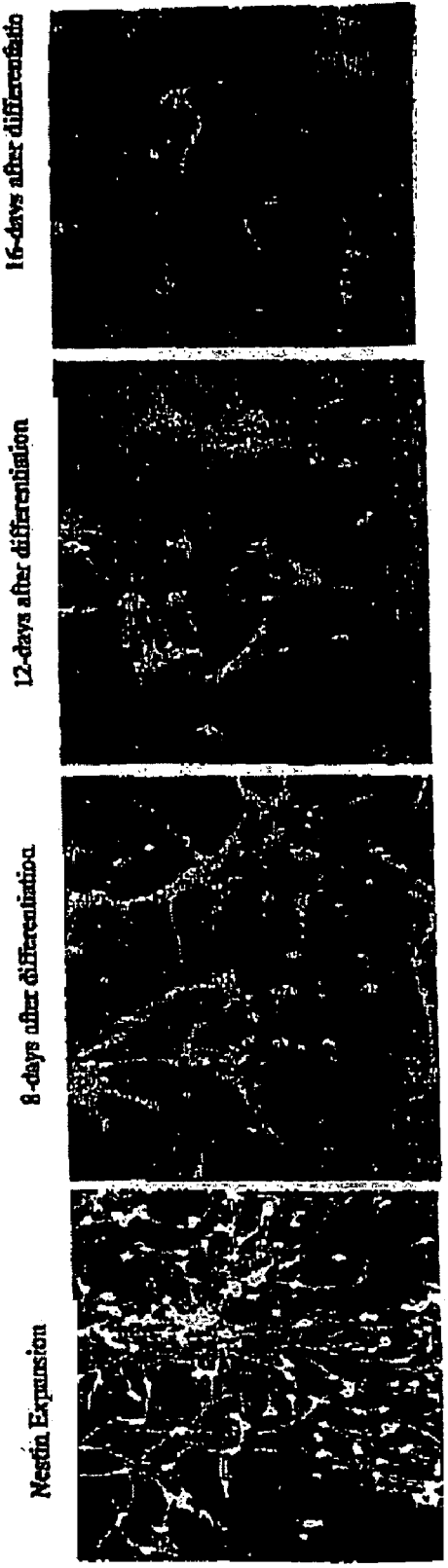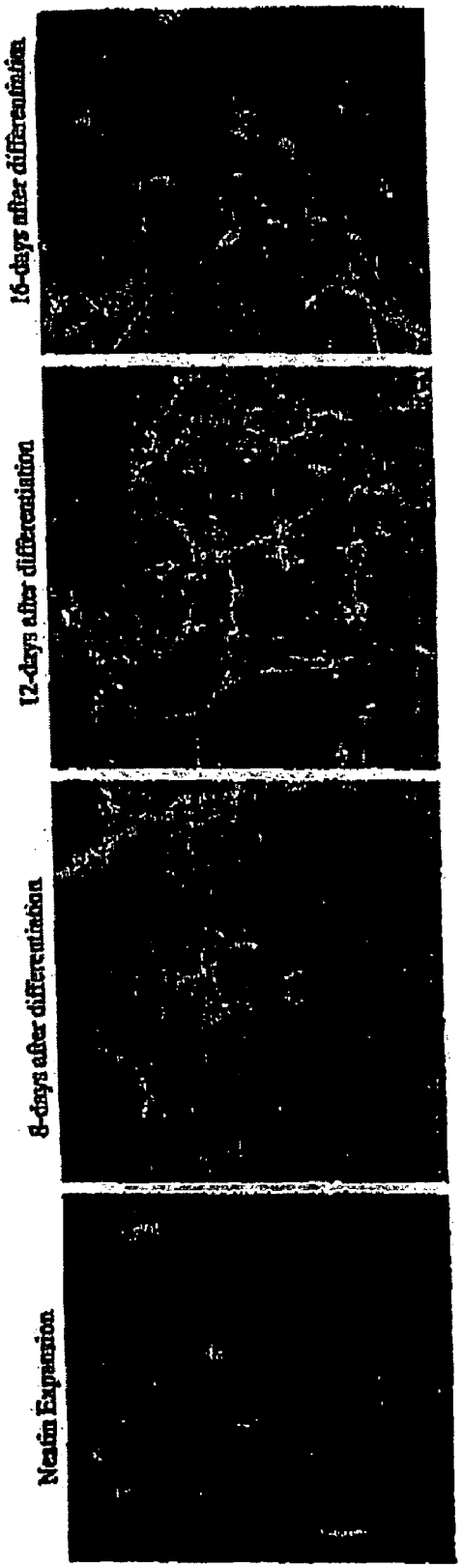
Figure-3c
Glutamate immunolabeled cells
GABA immunolabeled cells

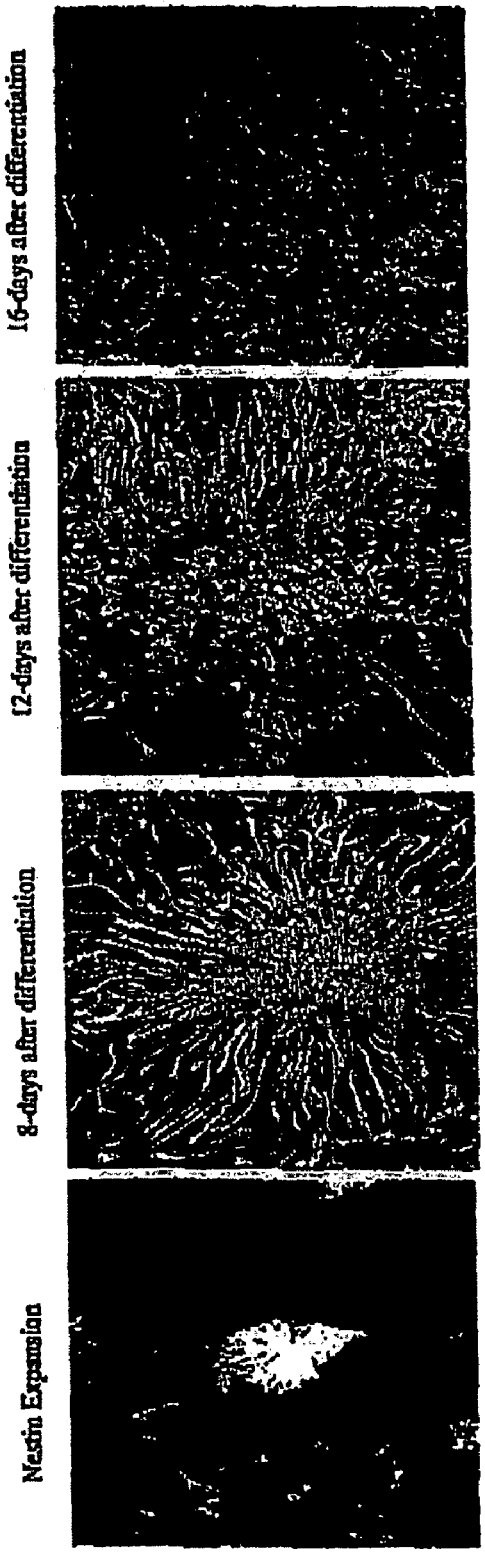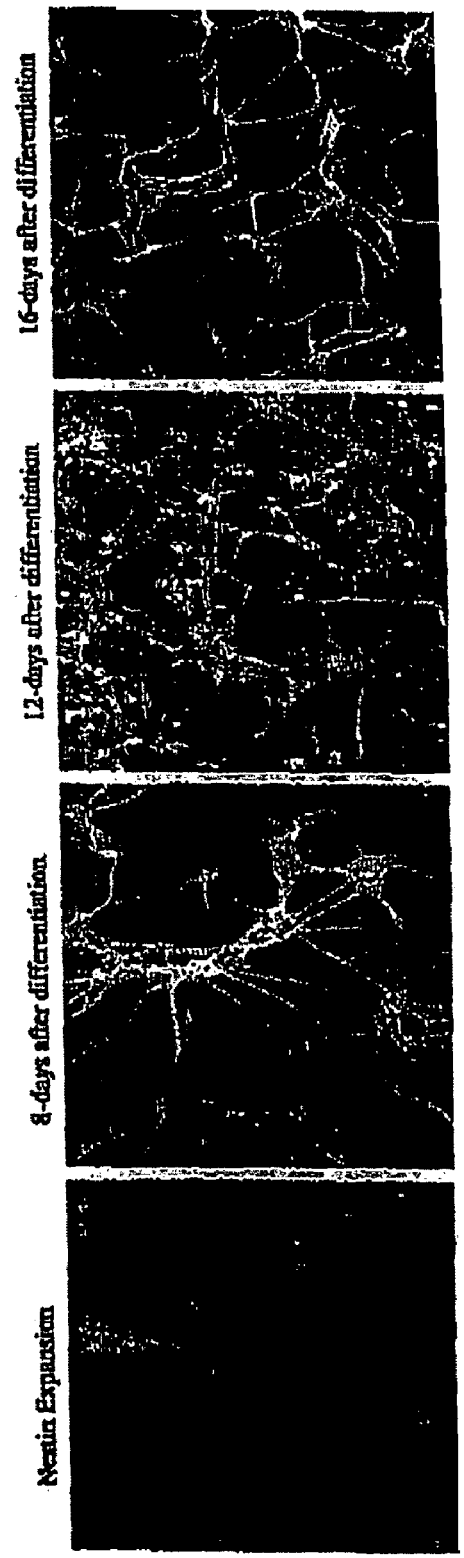
Figure-3d
Nestin immunolabeled cells / MAP-2 immunolabeled cells Co-localization of GAD-65/67 and GABA

Neuronal population derived from ES cells

1 = Total Neurons; 2 = Glutamate; 3 = GABA; 4 = TH, 5 = 5-HT

GABA estimation by HPLC

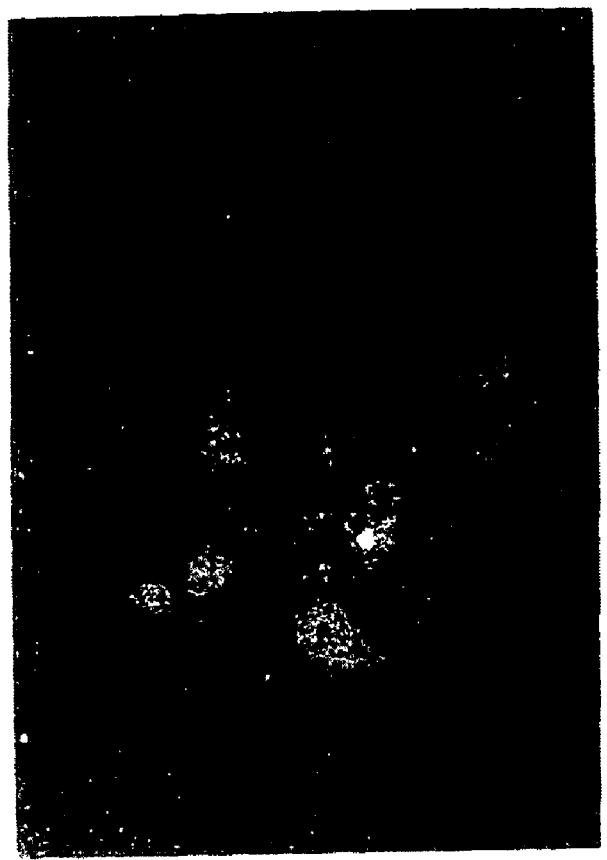
Figure 9: anti-GABA-B receptor
Figure 8: anti-GABA-A receptor

IN VITRO GENERATION OF GABAERGIC NEURONS FROM PLURIPOTENT STEM CELLS

CROSS-REFERENCES TO RELATED APPLICATIONS

Not applicable.

STATEMENT REGARDING FEDERALLY SPONSORED RESEARCH OR DEVELOPMENT

Not applicable.

REFERENCE TO A "MICROFICHE APPENDIX"

Not applicable.

BACKGROUND OF THE INVENTION

1. Field of the Invention

The present disclosure relates to an improved method of producing terminally differentiated neuronal cells such as GABAergic neurons from pluripotent stem cells such as murine embryonic stem cells or human embryonic stem cells. The GABAergic neurons generated according to the present disclosure may serve as an excellent source for cell replacement therapy in neurodegenerative disorders and neuronal diseases such as, for example, stroke, ischemia, Parkinson's disease, Alzheimer's disease, epilepsy, and Huntington's disease.

2. Description of Related Art

Gamma aminobutyric acid (GABA) is the principal inhibitory neurotransmitter in the central nervous system (CNS), and is widely distributed throughout the brain and expressed in interneurons modulating local circuits. GABAergic neurons, which produce GABA, are the predominant inhibitory neurons in the mammalian CNS, and approximately 60-75% of all synapses in the CNS are GABAergic (Schwartz, R. D., 1988, Biochem. Pharmacol. 37:3369-75). GABAergic neurons are localized in the hippocampus, cerebellum, cerebral cortex, and hypothalamus, and GABA binds to at least three receptors, including GABA-A and GABA-B. GABA-A receptors mediate fast inhibitory synaptic transmissions, neuronal excitability, and rapid changes in mood, such as seizure threshhold, anxiety, panic, and response to stress (i.e., the "fight or flight" response). GABA-A receptors are also binding sites for benzodiazepines, ethanol, barbiturates, and neurosteroids. GABA-B receptors mediate slow inhibitory transmissions, and may be important in memory, mood, and pain.

The pathogenesis of several neurological disorders appears to involve a decrease in GABAergic neurotransmission, including some forms of epilepsy, chronic pain, anxiety, and other mood disorders. For example, a positron emission tomography (PET) study showed that patients with panic disorder have decreased GABA-A receptor binding (Malizia et al., 1998, Arch. Gen. Psychiatry 55:715-20). In addition, low plasma GABA may be characteristic of a subgroup of patients with mood disorders (Brambilla et al., 2003, Mol. Psychiatry 8:721-37). Certain drugs that enhance GABA activity have been shown effective in the treatment of these disorders, such as benodiazepines, valproate, and phenobarbital.

Many diseases of the central nervous system (CNS) such as Parkinson's disease, Alzheimer's disease, Multiple sclerosis, Huntington's disease, amyotrophic lateral sclerosis, cerebral ischemia, and stroke are characterized by degeneration of neurons in the brain and spinal cord regions. Cells or neurons that degenerate or are otherwise damaged are not intrinsically replaced or repaired by the body, which can lead to permanent and irreversible damage (During et al., 2001, Human Gene Ther. 12:1589-1591). Stroke or cerebral ischemia can occur when a blood clot blocks a blood vessel or artery, interrupting blood flow to an area of the brain, which causes the death of brain cells in the immediate area of the block. The brain cells in the infarct usually die within minutes to a few hours after the stroke or ischemia occurs. The death of these cells can lead to a release of chemicals that set off a chain reaction called the "ischemic cascade," which endangers brain cells in the larger, surrounding area of brain tissue for which the blood supply is compromised. Without prompt medical treatment, this larger area of brain cells may also die, which can cause even more severe and long-term damage to the brain. Given the rapid pace of the ischemic cascade, the "window of opportunity" for interventional treatment is only about six hours. Beyond this window of time, reestablishment of blood flow and administration of neuroprotective agents may fail to help and can potentially cause further damage to brain functions (Padosch et al., 2001, Anaesthesist 50:905-920; Nishino and Borlongan, 2000, Prog. Brain Res. 127:461-476).

When stroke occurs, the disruption of blood flow to the brain has a detrimental and potentially fatal effect on individual or groups of neurons. Starving large numbers of neurons of oxygen and vital nutrients in a specific area of the brain due to cerebral ischemia can lead to severe loss of functional capabilities in patients. For example, stroke patients may experience loss of speech, memory, cognition, reduced mobility, or even paralysis. Without an adequate blood supply, brain cells lose their ability to produce energy, particularly adenosine triphosphate (ATP). If critical thresholds of this energy failure occur, brain cells are damaged and die. Many researchers believe that an immense number of mechanisms cause brain cell damage and death following energy failure, with each of these mechanisms representing a potential route for therapeutic intervention.

One way brain cells respond to energy failure is by elevating the concentration of intracellular calcium. These concentrations can be driven to dangerous levels by a process called excitotoxicity, in which brain cells release excessive amounts of glutamate, a neurotransmitter, which leads to the degradation and destruction of vital cells located in the hippocampus, cortex, and thalamus region of the brain (Nishino and Borlongan, 2000, Prog. Brain Res. 127:461-476). In addition, GABA-producing cells in the hippocampus region of the brain often degenerate after a stroke (Nishino and Borlongan, 2000, Prog. Brain Res. 127:461-476). Based on neurohistopathological and neuropsychological investigations, several neuroprotective drug therapies have been developed to treat neurological disorders associated with cerebral ischemia or stroke, such as GABAergic agonists, calcium antagonists, glutamate antagonists, and antioxidants (Stutzmann et al., 2002, CNS Drug Rev. 8:1-30; Rochelle et al., 2001, J. Neurochem. 77:353-371; Blezer et al., 2002 Eur. J. Pharmacol. 444:75-81). Currently there are hundreds of drugs and compounds in various stages of development for the prevention and acute interventional treatment of stroke (Rochelle et al., 2001, J. Neurochem. 77:353-371). It is anticipated that several of these drugs will be submitted to the FDA for approval, and many are already engaged in the last phase of clinical trials. Among these, GABAergic drugs are found to be exceptionally effective in treating neurological disorders associated with cerebral ischemia or stroke.

Given the multi-dimensional nature of ischemic brain cell injury, however, stroke experts predict that no single drug-based therapy will be able to completely protect the brain during and after a stroke. Since current therapeutic alternatives do not adequately treat damage associated with cerebral ischemia or stroke, there is great interest in developing alternative therapies for various neurodegenerative disorders and neuronal diseases. A cell-based therapy may be the only means available for comprehensively treating the damage caused by such an event. Many neurological diseases and conditions are caused by the loss of neuronal cells in the brain and spinal cord regions. A wide spectrum of these neurological diseases and conditions, including but not limited to Parkinson's disease, Alzheimer's disease, Huntington's disease, and spinal cord injury, may be treatable with cell based therapies. For example, patients with Parkinson's disease have been successfully treated by transplanting dopaminergic neurons into the brain of affected individuals (Grisolia, 2002, Brain Res Bull 57:823-826). Therefore, when GABA-producing cells are affected or damaged in cerebral ischemia or stroke patients, the replacement of these damaged GABA-producing cells with new and healthy GABA-producing cells would be an ideal therapy for the treatment of cerebral ischemia or stroke.

One major problem with cell transplantation as a therapeutic option for neurodegenerative disorders and neuronal diseases is the need for large quantities of neuronal cells, which are difficult to isolate from fetal or adult sources. One solution to this dilemma is the availability of pluripotent stem cells, which can be used to generate unlimited numbers of terminally differentiated cell types. Pluripotent embryonic stem (ES) cells are a viable alternative source of neuronal cells that may be used to treat various neurodegenerative disorders and neuronal diseases. ES cells can proliferate indefinitely in an undifferentiated state and are pluripotent, which means they are capable of differentiating into nearly all cell types present in the body. Because ES cells are capable of becoming almost all of the specialized cells of the body, they have the potential to generate replacement cells for a broad array of tissues and organs such as heart, pancreas, nervous tissue, muscle, cartilage, and the like. ES cells can be derived from the inner cell mass (ICM) of a blastocyst, which is a stage of embryo development that occurs prior to implantation. Human ES cells may be derived from a human blastocyst at an early stage of the developing embryo lasting from the 4th to 7th day after fertilization. ES cells derived from the ICM can be cultured in vitro and under the appropriate conditions proliferate indefinitely.

ES cell lines have been successfully established for a number of species, including mouse (Evans et al., 1981, Nature 292:154-156), rat (Iannaccone et al., 1994, Dev. Biol., 163: 288-292), porcine (Evans et al., 1990, Theriogenology 33:125-128; Notarianni et al., 1990, J. Reprod. Fertil. Suppl. 41:51-6), sheep and goat (Meinecke-Tillmann and Meinecke, 1996, J. Animal Breeding and Genetics 113:413-426; Notarianni et al., 1991, J. Reprod. Fertil. Suppl. 43:255-60), rabbit (Giles et al., 1993, Mol. Reprod. Dev. 36:130-138; Graves et al., 1993, Mol. Reprod. Dev. 36:424-433), mink (Sukoyan et al., Mol. Reprod. Dev. 1992, 33:418-431), hamster (Doetschman et al., 1988, Dev. Biol. 127:224-227), domestic fowl (Pain et al., 1996, Development 122(8):2339-48), primate (U.S. Pat. No. 5,843,780), and human (Thomson et al., 1998, Science 282:1145-1147; Reubinoff et al., 2000, Nature Biotech. 18:399-403). Like other mammalian ES cells, human ES cells differentiate and form tissues of all three germ layers when injected into immunodeficient mice, proving their pluripotency. Published reports show that human ES cells have been maintained in culture for more than a year during which time they retained their pluripotency, self-renewing capacity, and normal karyotype (Thomson et. al., 1995, PNAS 92:7844-7848).

ES cells have been shown to differentiate into neurons and glial cells in both in vitro models (Bain et al., 1995, Dev. Biol. 168:342-357), as well as in vivo models (Brustle, et al., 1999, Science 285:754-56). Similarly, blastula-stage stem cells can differentiate into dopaminergic and serotonergic neurons after transplantation (Deacon et al., 1998, Exp. Neurol. 149: 28-41). Human or rodent stems cells are able to differentiate into specific neuronal types when grafted into either a developing central nervous system (Flax et al., 1998, Nat. Biotechnol. 16:1033-39; Brustle et al., 1998, Nat. Biotechnol. 16:1040-44; Reubinoff et al., 2001, Nat. Biotechnol. 19:1034-40) or neurogenic areas of the adult CNS (Fricker et al., 1999, J. Neurosci. 19:5990-6005; Shihabuddin et al., 2000, J. Neurosci. 20:8727-35).

One method for generating GABA-producing cells from immature neuronal cells has been reported (Rubenstein et al., U.S. Pat. No. 6,602,680, incorporated herein by reference). Rubenstein et al. reported the production of GABAergic cells by increasing the activity of a DLX gene, for example DLX1, DLX2, or DLX5, in an immature neuronal cells. The increase in DLX activity causes differentiation of the immature neuronal cells into cells with the GABAergic phenotype. Methods for deriving GABA-producing cells from mouse embryonic stem cells have also been reported (Hancock et al., 2000, Biochem. Biophys. Res. Commun. 271(2):418-21, Westmoreland et al., 2001, Biochem. Biophys. Res. Commun. 284 (3):674-80; U.S. Publication No. 2003/0036195 A1, each specifically incorporated herein by reference), but these methods do not generate high percentages of GABAergic neurons. Since large numbers of GABAergic neurons are required for cell replacement therapy, there is a need for additional in vitro methods for generating large numbers of GABAergic neurons from pluripotent stem cells.

Methods that can generate high yields of GABAergic neurons have great clinical significance for cell transplantation therapy, particularly for patients suffering from cerebral ischemia or stroke. To date, available therapies are extremely limited for treating the neuropathology associated with cerebral ischemia and stroke, so there is great interest in developing alternative therapies. Cell-based therapies will require large numbers of cells or neurons for treatment, which is not possible if fetal or adult tissue is the only source available for the cells and neurons. For example, about 1 million dopaminergic producing cells must be transplanted into a single Parkinson's disease animal model to study the functional recovery of motor function (Grisolia, 2002, Brain Res. Bull. 57:823-826). Obtaining such a large number of cells using fetal material raises many ethical problems. Generation of GABAergic neurons from pluripotent stem cells offers a potentially unlimited supply of GABAergic neurons to use in cell based-therapies. But methods that yield high percentages of GABAergic neurons are necessary to make this source practical, particularly since it is likely that large numbers of GABAergic neurons will be needed for therapeutic methods utilizing these cells.

BRIEF SUMMARY OF THE INVENTION

The present disclosure relates to improved methods of producing neuroprogenitor cells, as well as terminally differentiated neuronal cells or glial cells, from pluripotent stem cells such as embryonic stem (ES) cells. In a preferred embodiment, the pluripotent stem cells or ES cells are murine cells. The cells generated herein include but are not limited to cells with the phenotypic characteristics of neuroprogenitor cells, neuronal cells such as GABAergic, dopaminergic, serotonergic, and glutamatergic neurons, as well as glial cells such as oligodendrocytes and astrocytes. The present disclosure demonstrates that pluripotent stem cells, for example murine ES cells, can differentiate into a high proportion of GABAergic neurons (e.g., at least about 60%). The percentage of GABAergic neurons generated according to the methods of the present disclosure is higher than previously described methods. GABAergic neurons can be utilized for multi-potential cell-based therapies, for example cell replacement therapy, or to treat neurodegenerative disorders and neuronal diseases, including, for example, stroke, cerebral ischemia, epilepsy, Parkinson's disease, Huntington's disease, Alzheimer's disease, chronic pain, anxiety, and other mood disorders.

The present disclosure provides a differentiated cell population in an in vitro culture obtained by differentiating pluripotent stem cells, wherein at least 60% of the differentiated neural cells are GABAergic neurons, cells that exhibit GABAergic neuron phenotypes, or cells that produce gamma aminobutyric acid (GABA). Preferably the GABAergic neurons express GAD65, GAD67, GABA-A receptor, or GABA-B receptor, or a combination thereof. In other embodiments, at least about 30%, 35%, 40%, 45%, 50%, 55%, 65%, 70%, 75%, 80%, 85%, 90%, 95% or 99% of the differentiated cells are GABAergic neurons or produce GABA. Preferably, the GABAergic neurons or cells that produce GABA are derived from ES cells, more preferably human or murine ES cells. In other embodiments, the differentiated cell population also comprises at least about 15% dopaminergic neurons, at least about 10% glutamatergic neurons, at least about 5% serotonergic neurons, at least about 5% oligodendrocytes, at least about 5% astrocytes, or a combination of these amounts.

The present disclosure also provides methods for generating differentiated cell populations from pluripotent stem cells comprising the following steps:
  (a) expanding a culture of pluripotent stem cells;
  (b) culturing the pluripotent stem cells to select for neuroprogenitor cells that are positive for nestin;
  (c) expanding the nestin-positive neuroprogenitor cells; and
  (d) differentiating the nestin-positive cells to generate a differentiated cell population by culturing the cells in a differentiation media which comprises cytosine β-d-Arabino furanoside (Ara-C).

In a preferred embodiment, the pluripotent stem cells are ES cells, more preferably human or murine ES cells.

In other embodiments, the above methods further include the step of culturing the pluripotent stem cells of step (b) to form embryoid bodies. Preferably, these embryoid bodies are cultured under conditions which select for neuroprogenitor cells that are positive for nestin, for example by culturing the pluripotent stem cells or embryoid bodies in serum-free medium, preferably for 6-10 days. In preferred embodiments, the serum-free medium is ITSFn serum-free defined medium, which preferably includes one or more soluble factors selected from the group consisting of insulin, sodium selenite, basic fibroblast growth factor, transferrin, and fibronectin. Preferably, the ITSFn serum-free defined medium comprises insulin, sodium selenite, transferrin, and fibronectin. In preferred embodiments, these methods will generate neuroprogenitor cells which preferably comprise at least about 60-75% nestin-positive cells, more preferably about 80-90% nestin-positive cells, and most preferably about 95-99% nestin-positive cells.

In certain embodiments, the above methods further include the step of expanding the nestin-positive neuroprogenitor cells of step (c) in CNS expansion media, preferably for 6-10 days. Preferably, the CNS expansion media comprises one or more soluble factors selected from the group consisting of N2 supplement, B27 supplement, and a neural-inducing agent. In a preferred embodiment, the neural-inducing agent is basic fibroblast growth factor (bFGF). In another preferred embodiment, the nestin-positive neuroprogenitor cells are plated on a culture dish pre-coated with poly-L-ornithine, poly-L-laminin, or a combination of the two. The nestin-positive neuroprogenitor cells may be expanded in culture and serially passed for one or more population doublings. These cells may also be cryopreserved in liquid nitrogen.

The nestin-positive neuroprogenitor cells are preferably grown in differentiation media for 2 or more days as set forth in step (d) of the above methods. Preferably, the differentiation media also comprises N2 supplement, B27 supplement, or both, but not basic fibroblast growth factor (bFGF). In preferred embodiments, after the neuroprogenitor cells are grown in the differentiation media which contains cytosine β-d-Arabino furanoside (Ara-C), the cells are further cultured in differentiation media without Ara-C, preferably for 8-16 days, more preferably for 12 days.

The present disclosure also provides methods of generating GABAergic neurons from neuroprogenitor cells, comprising enriching the neuroprogenitor cells for cells that are positive for nestin, and differentiating the nestin-positive cells to generate GABAergic neurons by culturing the cells in the presence of Ara-C. After the nestin-positive cells are cultured in differentiation media with Ara-C, they are preferably further differentiated in differentiation media without Ara-C. Preferably, at least about 40-99% of the nestin-positive cells differentiate into GABAergic neurons using these methods.

In preferred embodiments, the methods disclosed above are used to generate differentiated cell populations, which preferably comprise about 60-80% GABAergic neurons, more preferably about 75-90% GABAergic neurons, and most preferably about 95-99% GABAergic neurons. In other embodiments, these methods are used to generate differentiated cell populations, which preferably comprise about 15-30% dopaminergic neurons, more preferably about 20-40% dopaminergic neurons, and most preferably about 25-50% dopaminergic neurons. In certain embodiments, these methods are used to generate differentiated cell populations, which preferably comprise about 5-20% serotonergic or glutamatergic neurons, more preferably about 10-25% serotonergic or glutamatergic neurons, and most preferably about 15-30% serotonergic or glutamatergic neurons. In other embodiments, these methods are used to generate differentiated cell populations, which preferably comprise about 5-20% oligodendrocytes or astrocytes, more preferably about 10-25% oligodendrocytes or astrocytes, and most preferably about 15-30% oligodendrocytes or astrocytes.

The present disclosure further provides an in vitro transplantation model to study the efficacy, survivability, and functionality of differentiated cells, preferably neuronal or neural cells, in a host-like environment, such as a brain environment. For example, GABAergic neurons described herein are cultured with adult brain cells, preferably neural or hippocampal cells. Preferably the GABAergic neurons are plated onto the adult hippocampal cells. The cells are cultured together for at least 3-20 days, more preferably 1 week, and the survival of the neuronal or neural cells is determined. Preferably at least about 80% of the neuronal or neural cells survive, more preferably 90-99% of the cells survive. A high survival rate indicates that the cells are likely to function in an adult brain environment, and may be used to treat neurodegenerative disorders or neuronal diseases.

The present disclosure also provides methods for treating subjects with neurodegenerative disorders or neuronal diseases by administering to a subject neuroprogenitor cells or differentiated neuronal cells derived from pluripotent stem cells, for example murine or human ES cells, as described herein. The cells derived herein may also be used for cell replacement therapy in the subject. For example, a differentiated neuronal cell population may be derived as follows:

(a) expanding a culture of pluripotent stem cells;
(b) culturing the pluripotent stem cells to select for neuroprogenitor cells that are positive for nestin;
(c) expanding the nestin-positive neuroprogenitor cells; and
(d) differentiating the nestin-positive cells to generate a differentiated cell population by culturing the cells in a differentiation media which comprises cytosine β-d-Arabino furanoside (Ara-C).

In another preferred embodiment, the differentiated cells of step (d) are further differentiated in differentiation media without Ara-C. In preferred embodiments, the subject is a patient, more preferably a human patient. Preferably the neuroprogenitor cells or differentiated neuronal cells derived from pluripotent stem cells are histocompatible with the subject, for example if the neuroprogenitor cells or differentiated neuronal cells have essentially the same genome as the subject.

In certain embodiments, GABAergic, dopaminergic, serotonergic, and glutamatergic neurons, as well as glial cells such as oligodendrocytes and astrocytes, are isolated from the differentiated neuronal cell population and administered to the patient. In a preferred embodiment, GABAergic neurons are administered to the subject. These cells, as well as neuroprogenitor or differentiated neuronal cell populations, can be administered to the subject to treat a variety of neurodegenerative disorders or neuronal diseases, including but not limited to stroke, cerebral ischemia, epilepsy, Parkinson's disease, Huntington's disease, Alzheimer's disease, spinal cord injury, amyotrophic lateral sclerosis (ALS), epilepsy, and other CNS disorders, as well as chronic pain, anxiety, and other mood disorders. These subjects may also be treated by cell replacement therapy. Preferably the cells are administered by transplantation, for example by transplanting the desired cells into the brain of the subject.

Another embodiment of the present disclosure is a method of treating a subject with a neurodegenerative disorder or neuronal disease comprising the following steps:

(a) expanding a culture of pluripotent stem cells;
(b) culturing the pluripotent stem cells to select for neuroprogenitor cells that are positive for nestin;
(c) expanding the nestin-positive neuroprogenitor cells;
(d) differentiating the nestin-positive cells to generate a differentiated neural cell population by culturing the cells in a differentiation media which comprises cytosine β-d-Arabino furanoside (Ara-C); and
(e) transplanting a therapeutically effective amount of the differentiated neural cell population into the central nervous system of the patient.

In a preferred embodiment, the pluripotent stem cells are murine or human ES cells. In other preferred embodiments, subject is a patient, more preferably a human patient. Preferably the differentiated neural cell population is histocompatible with the patient. In another embodiment, step (d) further comprises differentiating the cells in the differentiation media for 2 or more days, and subsequently differentiating the cells in a second differentiation media that does not contain cytosine β-d-Arabino furanoside (Ara-C). In preferred embodiments, GABAergic neurons are isolated from the differentiated neural cell population and administered to the subject, for example to the brain of the subject, preferably by transplantation. In certain embodiments, the neurodegenerative disorder or neuronal disease is selected from the group consisting of Parkinson's disease, Alzheimer's disease, Huntington's disease, Lewy body dementia, multiple sclerosis, cerebellar ataxia, progressive supranuclear palsy, spinal cord injury, amyotrophic lateral sclerosis (ALS), epilepsy, stroke, and ischemia.

In other embodiments, the neuroprogenitor cell population or differentiated neuronal cells derived from pluripotent stem cells as described herein can be used to screen compounds, for example small molecules and drugs, for their effect on the cell population, particular differentiated neural or glial cells, or the activity of these cells. The compounds can also be screened for neural cell toxicity or modulation. For example, a compound can be evaluated by adding the compound to a population of differentiated neural cells, such as GABAergic neurons, and comparing the survival, morphology, phenotype, functional activity, or other characteristics of the cells with differentiated neural cells cultured under similar conditions but not exposed to the compound. The compounds can be screened, for example, to determine whether they effect changes in neurotransmitter synthesis, release, or uptake by the cells.

Another embodiment of the present disclosure is a method of generating an in vitro transplantation model for neural cells, comprising the following steps:

(a) isolating adult hippocampal cells;
(b) dissociating and culturing the hippocampal cells to generate a hippocampal cell culture; and
(c) culturing neural cells on the hippocampal cell culture;

wherein the survival of the neural cells on the hippocampal cell culture is evaluated. In other embodiments, synaptic formation between the neural cells and the hippocampal cell culture are evaluated. In one embodiment of the present disclosure, the adult hippocampal cells are isolated from a mouse. In certain embodiments, the neural cells cultured on the hippocampal cell culture are, for example, GABAergic, dopaminergic, serotonergic, or glutamatergic neurons. In other embodiments, glial cells such as oligodendrocytes and astrocytes are cultured on the hippocampal cell culture. The neural cells or glial cells cultured on the hippocampal cell culture may be derived using the methods disclosed herein, or by derived or isolated by other methods well known to those of skill in the art. Preferably, at least about 50% of the neural cells cultured on the hippocampal cell culture survive for at least a week, more preferably about 60%, 70%, 80%, 90%, or 95%. In one preferred embodiment, greater than about 90% of GABAergic neurons survive after one week of culture.

BRIEF DESCRIPTION OF THE SEVERAL VIEWS OF THE DRAWINGS

The following drawings form part of the present specification and are included to further demonstrate certain aspects of the present disclosure, the inventions of which can be better understood by reference to one or more of these drawings in combination with the detailed description of specific embodiments presented herein.

FIG. 1 shows a diagrammatic representation of the derivation of GABAergic neurons from murine ES cells, as well as in vitro transplantation of the GABAergic neurons with hippocampal neurons derived from adult murine brain.

FIG. 2 shows a diagrammatic representation of the steps for murine ES cell differentiation into terminally differentiated neuronal cells, which includes: (1) expansion of undifferentiated cells; (2) formation of embryoid bodies; (3) selection of nestin-positive cells; (4) expansion of nestin-positive cells; and (5) differentiation of neural progenitors into terminally differentiated neuronal cells.

FIG. 3 shows the localization of the following markers by immunoreactivity in the neuronal population derived from murine ES cells: (a) GAD-65 and GAD-67; (b) GAT-1 and GAT-2; (c) Glutamate and GABA; and (d) Nestin and MAP-2. The immunoreactivity was studied in 4 different stages: expansion of nestin-positive cells, and 8, 12, and 16 days after differentiation.

FIG. 8 shows immunoreactivity of cells derived from murine ES cells using the methods disclosed herein after 12 days of differentiation with anti-GABA-A receptor antibodies. Approximately 80% of the cells were positive for immunofluorescence with anti-GABA-A receptor antibodies.

FIG. 9 shows immunoreactivity of cells derived from murine ES cells using the methods disclosed herein after 12 days of differentiation with anti-GABA-B receptor antibodies. Approximately 25% of the cells were positive for immunofluorescence with anti-GABA-B receptor antibodies.

DETAILED DESCRIPTION OF THE INVENTION

Figure 4:
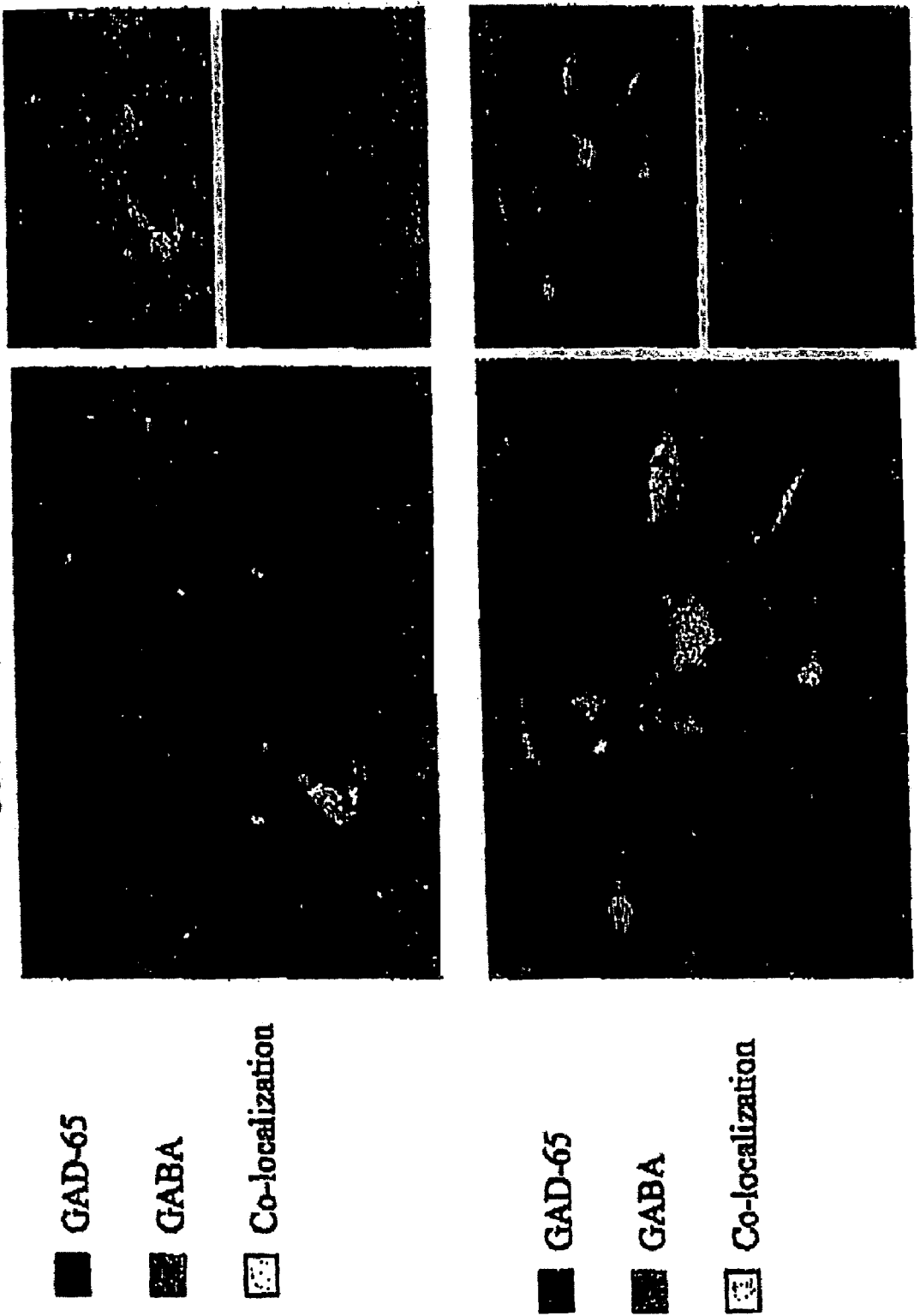
FIG. 4 shows co-localization of GABA and GAD-65/GAD-67 immunoreactivity in GABAergic neurons derived from murine ES cells using the methods disclosed herein. The presence of GABA immunofluorescence in the GAD-65 and GAD-67 positive cells confirms that these GABAergic neurons produce GABA.

The present disclosure provides methods for the efficient generation of cells of neural lineage that are differentiated from pluripotent stem cells. The cells generated herein include but are not limited to cells with the phenotypic characteristics of neuroprogenitor cells, GABAergic, dopaminergic, serotonergic, and glutamatergic neurons, as well as glial cells such as oligodendrocytes and astrocytes. Cells generated herein are identified by phenotypic characteristics, morphological characteristics, and/or cell markers, which are readily appreciated by those of skill in the art of evaluating such cells. As used herein, the term "neuroprogenitor cells" is interchangeable with the terms neural or neuronal progenitor cells, as well as neural or neuronal precursor cells, and refers to a cell that can generate progeny that are either neuronal cells, such as neuronal precursors, neural cells, or neurons, or glial cells, such as glial precursors, astrocytes, or oligodendrocytes. The methods disclosed herein involve culturing cells in a combination of soluble factors and environmental conditions which encourage the cells to differentiate into cells of neural lineage. The methods disclosed herein are preferably used to derive GABAergic neurons from pluripotent stem cells.

These precursor and differentiated neural cells can be used for a number of applications, including therapeutic and experimental applications, as well as in vitro drug development and screening, such as screening a compound for neural cell toxicity or the ability to modulate the function of neuronal cells. Generation of precursor and differentiated neural cells such as GABAergic neurons, as well as other specialized neuronal cell types, from pluripotent stem cells offers a potentially unlimited supply of these neurons, with tremendous potential benefit to individuals suffering from debilitating neurodegenerative disorders and neuronal diseases, including but not limited to stroke, ischemia, Huntington's disease, epilepsy, chronic pain, anxiety, and other mood disorders. The precursor and differentiated neural cells described herein are typically the progeny of the cell population from which they were derived, and therefore will have essentially the same genome as the parent population, including a parent population that has been genetically altered, transformed, or transfected.

A preferred embodiment of the present disclosure is directed to improved methods for generating GABAergic neurons from pluripotent stem cells, preferably mammalian embryonic stem (ES) cells or mammalian embryonic germ (EG) cells. In particularly preferred embodiments, the mammalian ES or EG cells are murine or human ES cells or EG cells. These neurons are derived from pluripotent stem cells by culturing the cells in the presence of certain soluble factors and environmental conditions.

As used herein, the term "GABAergic neurons" refer to neuronal cells that express, produce, or secrete the neurotransmitter GABA. Preferably, the terminal differentiation of GABAergic neurons involves the activation and regulation of the genes required for GABA synthesis, as well as vesicular packaging and release. In other preferred embodiments, GABAergic neurons express both the GABA-A and GABA-B receptors. GABA belongs to the chemical family glutamic acid decarboxylase (GAD), and GAD is the key enzyme in the synthesis of GABA. Mammalian species express two isoforms of GAD designated GAD1 and GAD2, which are expressed at various levels in different brain regions. GAD1 and GAD2 are also known as GAD67 and GAD65 respectively, which is indicative of their relative molecular masses in kDa. Since GAD65 and GAD67 are the enzymes that synthesize GABA, they both can be used as markers for identifying GABAergic neurons. In addition, the vesicle inhibitory amino acid transporter (VIAAT) is required for the synaptic packaging of GABA, and is also a marker for identifying GABAergic neurons. The pathogenesis of several neurodegenerative disorders and neuronal diseases appears to involve the loss of GABAergic neurons or a decrease in GABAergic neurotransmission, including some forms of stroke, ischemia, Huntington's disease, epilepsy, chronic pain, anxiety, and other mood disorders.

The present disclosure is directed to improved methods of differentiating pluripotent stem cells into neuroprogenitor cells, as well as into a differentiated population of neural cells having phenotypic, molecular, and/or cellular characteristics similar to cells of neural lineage. In a preferred embodiment, the pluripotent stem cells are murine or human ES cells, which are differentiated into neural cells, preferably GABAergic neurons, using specific culture conditions. The present disclosure also relates to cells and cell populations produced by the disclosed methods. In certain embodiments, the disclosed methods comprise the following steps:

1. A population of pluripotent stem cells are isolated; the pluripotent stem cells are preferably murine or human ES cells.
2. The pluripotent stem cells are expanded to provide sufficient starting material.
3. The pluripotent stem cells are cultured in suspension to generate embryoid bodies.
4. The embryoid bodies are replated on a substrate and incubated in a serum-free medium which selects for neuroprogenitor cells.
5. The neuroprogenitor cells are expanded in an expansion medium, which comprises soluble factors related to the nervous system.
6. The neuroprogenitor cells are differentiated into mature neurons in differentiation medium, preferably the medium comprises a combination of soluble factors related to the nervous system, as well as cytosine β-d-Arabino furanoside (Ara-C).

Sources of Pluripotent Stem Cells

The methods disclosed herein for the differentiation of cells of neural lineage from pluripotent stem cells involve the use of specific culture conditions, which direct differentiation of a remarkably high proportion of pluripotent stem cells into specific neuronal cell types. Pluripotent stem cells are derived from pre-embryonic, embryonic, or fetal tissues any time after fertilization, which, under the appropriate conditions, are able to differentiate into several different cell types that are derivatives of all three germ layers (endoderm, mesoderm, and ectoderm). Cells of neural lineage can also be derived from stem cells isolated from fetal or adult tissue that have the capacity to differentiate or be reprogrammed into cells of neural lineage. Pluripotent stem cells include but are not limited to mammalian ES cell and EG cells, preferably murine ES or EG cells, or primate or human ES cells and EG cells. Preferably, the undifferentiated pluripotent stem cells have the capacity to divide and proliferate indefinitely in culture. As used herein, the term "differentiation" refers to a process whereby undifferentiated pluripotent stem cells or precursors cells acquire a more specialized fate. For example, a differentiated cell has a phenotype which is characteristic of a particular cell type or tissue.

In a preferred embodiment, the ES cells and ES cell lines used herein are derived from the inner cell mass of a blastocyst. These blastocysts may be isolated from recovered in vivo fertilized preimplantation embryos, or from in vitro fertilization (IVF), for example embryos fertilized by conventional insemination, intracytoplasmic sperm injection, or ooplasm transfer. Human blastocysts are obtained from couples or donors who voluntarily donate their surplus embryos. These embryos are used for research purposes after acquiring written and voluntary consent from these couples or donors. Alternatively, blastocysts may be derived by transfer of a somatic cell or cell nucleus into an enucleated oocyte of human or non-human origin, which is then stimulated to develop to the blastocyst stage. The blastocysts used may also have been cryopreserved, or result from embryos which were cryopreserved at an earlier stage and allowed to continue to develop into a blastocyst stage embryo. The development of both the blastocyst and the inner cell mass will vary according to the species, and are well known to those of skill in the art.

Murine ES cells may be derived in vitro from preimplantation embryos such as blastocysts using techniques well known to those of skill in the art, such as standard immunosurgery techniques (Evans et al., Nature 292:154-159, 1981; Martin, Proc. Natl. Acad. Sci. USA 78:7634-7638, 1981, each incorporated herein by reference). Mouse EG cells may be derived from fetal germ cells, again using methods well known to those of skill in the art (Matsui et al., Cell 70:841-847, 1992, incorporated herein by reference). To maintain mouse ES cells in an undifferentiated state, the cells are preferably cultured in the presence of leukemia inhibitory factor (LIF) on fibroblast feeder layers (Williams et al., Nature 336:684-687, 1988, incorporated herein by reference).

Primate or human ES cells may be derived from a blastocyst using standard immunosurgery techniques as disclosed in U.S. Pat. Nos. 5,843,780 and 6,200,806, Thomson et al. (Science 282:1145-1147, 1998) and Reubinoff et al. (Nature Biotech. 18:399-403, 2000), each specifically incorporated herein by reference. Although ES cells derived in any number of the ways known to one of skill in the art can be used in the disclosed methods, a preferred embodiment uses human ES cells derived by a unique method of laser ablation (U.S. Ser. No. 10/226,711, specifically incorporated herein by reference). In brief, this method isolates cells from the inner cell mass of a blastocyst through laser ablation of part of the zona pellucida and trophectoderm of the blastocyst, which forms an aperture or hole in the blastocyst through which cells of the inner cells mass can be aspirated. These cells can then be further cultured to establish ES cell lines. This technique is advantageous because it allows the isolation of cells of the inner cell mass without undergoing the conventional cumbersome procedure of immunosurgery. In addition, ES cell lines generated using this technique, in particular human ES cell lines, can be isolated in the absence of any animal generated antibodies and sera, which minimizes the risk of any transmission of animal microbes to the ES cell lines. In another embodiment, human EG cells are used that are derived from primordial germ cells present in human fetal material (U.S. Pat. No. 6,090,622, and Shamblott et al., 1998, Proc. Natl. Acad. Sci. USA. 95:13726-13731, each specifically incorporated herein by reference).

Preferably, ES cell lines can be maintained in culture in an undifferentiated state for a prolonged period of time, for example over one year, and maintain a normal euploid karyotype. Human ES cells may be morphologically identified by high nucleus to cytoplasm ratios, prominent nucleoli, and compact colony formation, with often distinct cell borders and colonies that are often flatter than mouse ES cells. Human ES cells are also preferably immunoreactive with markers for human pluripotent ES cells, for example SSEA-3, SSEA-4, GCTM-2 antigen, and TRA 1-60, as described by Thomson et al. (1998), Reubinoff et al. (2000), Buehr and Mclaren (1993), each specifically incorporated herein by reference. Preferably the human ES cells also express alkaline phosphatase, as well as OCT-4. In other embodiments, ES cells are able to form embryoid bodies under non-adherent culture conditions (U.S. Pat. Nos. 5,914,268 and 6,602,711, each incorporated herein by reference). These embryoid bodies can be used to derive differentiated derivatives of the endoderm, mesoderm, and ectoderm germ layers, as well as other desired cell lineages.

Pluripotent stem cells, particularly ES or EG cells, can be propagated continuously under culture conditions that maintain the cells in a substantially undifferentiated state. ES cells must be kept at an appropriate cell density and repeatedly dissociated and subcultured while frequently exchanging the culture medium to prevent them from differentiating. For general techniques relating to cell culture and culturing ES cells, the practitioner can refer to standard textbooks and reviews, for example: E. J. Robertson, "*Teratocarcinomas and embryonic stem cells: A practical approach*" ed., IRL Press Ltd. 1987; Hu and Aunins, 1997, Curr. Opin. Biotechnol. 8(2):148-53; Kitano, 1991, Biotechnology 17:73-106; Spier, 1991, Curr. Opin. Biotechnol. 2:375-79; Birch and Arathoon, 1990, Bioprocess Technol. 10:251-70; Xu et al., 2001, Nat. Biotechnol. 19(10):971-4; and Lebkowski et al., 2001, Cancer J. 7 Suppl. 2:S83-93; each specifically incorporated herein by reference.

Traditionally, ES cells are cultured in ES medium on a layer of feeder cells. Feeder cell layers are cells of one tissue type that are co-cultured with ES cells, and provide an environment in which the ES cells may grow without undergoing substantial differentiation. Methods for culturing ES cells on feeder layers are well known to those of skill in the art (U.S. Pat. Nos. 5,843,780 and 6,200,806, WO 99/20741, U.S. Ser. Nos. 09/530,346 and 09/849,022, WO 01/51616, each specifically incorporated herein by reference). The feeder layer preferably reduces, inhibits, or prevents differentiation of ES cells. Feeder layers are typically an embryonic fibroblast feeder layer of either human or mouse origin, for example mouse embryonic fibroblasts, human embryonic fibroblasts, human fibroblast-like cells or mesenchymal cells derived from human embryonic stem cells, or STO cells.

ES cells are preferably cultured in the presence of ES medium, which reduces, inhibits, or prevents the differentiation of the ES cells. Preferably, ES medium used to culture ES cells is supplemented with a nutrient serum, for example a serum or serum-based solution that supplies nutrients effective for maintaining the growth and viability of ES cells. The nutrient serum may be animal serum such as fetal bovine serum (FBS) or fetal calf serum (FCS) (U.S. Pat. Nos. 5,453,357, 5,670,372, and 5,690,296, incorporated herein by reference). As used herein, FBS may be used in place of FCS, and vice versa. The ES medium may also be serum-free (WO 98/30679, WO 01/66697, U.S. Ser. No. 09/522,030, each specifically incorporated herein by reference). An example of suitable ES medium with serum for culturing ES cells is Dulbecco's modified Eagle's medium (DMEM), without sodium pyruvate, with high glucose content (70-90%) (GIBCO), supplemented with FBS or FCS (10-30%), β-mercaptoethanol (0.1 mM), non-essential amino acids (1%), and L-Glutamine 2 mM, 4 ng/ml basic fibroblast growth factor (bFGF), 50 U/ml penicillin, and 50 μg/ml streptomycin. The ES medium may also include 1000 U/ml of Leukemia inhibitory factor (LIF). An example of suitable serum-free ES medium for culturing ES cells is 80% "KnockOut" Dulbecco's modified Eagle's medium (DMEM) (GIBCO), 20% KnockOut SR (a serum-free replacement, GIBCO), β-mercaptoethanol (0.1 mM), non-essential amino acids (1%), and L-Glutamine 1 mM.

ES cells may also be cultured under feeder-free culture conditions. Methods for culturing ES cells in a feeder-free culture are well known to those of skill in the art (U.S. Publ. No. 2002/0022268, WO 03/020920, U.S. Ser. No. 10/235,094, each specifically incorporated herein by reference). ES cells in a feeder-free culture are preferably grown on a suitable culture substrate, for example an extracellular matrix, such as Matrigel® (Becton Dickenson) or laminin. Feeder-free cultures also preferably use conditioned medium to support the growth of ES cells. Conditioned medium is prepared by culturing a first population of either murine embryonic fibroblasts or human embryonic fibroblast cells in a medium for a sufficient period of time to produce "conditioned" medium, which will support the culturing of ES cells without substantial differentiation. Alternatively, the feeder-free culture can combine an extracellular matrix with an effective medium that is added fresh to the culture without being conditioned by another cell type (U.S. Publ. No. 2003/0017589, specifically incorporated herein by reference).

Preparation of Neuroprogenitor Cells

Isolated pluripotent stem cells may be expanded and then subjected to culture conditions that cause them to differentiate into neuroprogenitor cells. For pluripotent stem cells to advance along the neural differentiation pathway, the cells are cultured according to differentiation protocols disclosed herein. The pluripotent stem cells are cultured on a suitable substrate in a differentiation nutrient medium that contains differentiation agents such as soluble factors and growth factors. Suitable substrates include but are not limited to solid surfaces coated with a positive-charge, for example poly-L-lysine or polyornithine, substrates coated with extracellular matrix components, for example fibronectin, laminin, PDGF, EGF, collagen V, human amniotic membrane, or Matrigel®, or a combination thereof. Preferred differentiation nutrient mediums are those that support the proliferation, differentiation, and survival of desired neural cell types, and may include one or more suitable differentiation agents. As used herein, the term "growth factor" refers to proteins that bind to receptors on the cell surface with the primary result of activating cellular proliferation and differentiation. Suitable soluble factors include but are not limited to neurotrophins, mitogens, stem cell factors, growth factors, differentiation factors (e.g., TGF-β Superfamily), TGF-β Superfamily agonists, neurotrophic factors, antioxidants, neurotransmitters, and survival factors. Many soluble factors are quite versatile, stimulating cellular division in numerous different cell types, while others are specific to particular cell types.

Suitable differentiation agents that specifically encourage the differentiation of neuronal cell types include but are not limited to progesterone, putrescine, laminin, insulin, sodium selenite, transferrin, neurturin, sonic hedgehog (SHH), noggin, follistatin, epidermal growth factor (EGF), any type of fibroblast growth factor, cytosine β-d-Arabino furanoside (Ara-C), growth and differentiation factor 5 (GDF-5), members of the neurotrophin family (nerve growth factor (NGF), neurotrophin 3 (NT-3), neurotrophin 4 (NT-4), brain derived neurotropic factor (BDNF)), transforming growth factor α (TGF-α), transforming growth factor beta-3 (TGF β3), platelet-derived growth factor (PDGF-AA), insulin-like growth factor (IGF-1), bone morphogenic proteins (BMP-2, BMP-4), glial cell derived neurotrophic factor (GDNF), midkine, ascorbic acid, dibutyryl cAMP, dopamine, and ligands to receptors that complex with gp130 (e.g., LIF, CNTF, SCF, IL-11, and IL-6). As used herein, the term "fibroblast growth factor" or "FGF" refers to any suitable fibroblast growth factor, derived from any organism that expresses such factors, and functional fragments thereof A variety of FGFs are known to those of skill in the art, and include but are not limited to, FGF-1 (acidic fibroblast growth factor), FGF-2 (basic fibroblast growth factor), FGF-3 (int-2), FGF-4 (hst/K-FGF), FGF-5, FGF-6, FGF-7, FGF-8, and FGF-9. Differentiation nutrient mediums may also contain additives that help sustain cultures of neural cells, for example N2 and B27 additives (Gibco). Preferably, the differentiation agents retinoic acid, 13-cis retinoic acid, and trans-retinoic acid are not used in any of the methods disclosed herein.

The first step of differentiating the pluripotent stem cells involves inducing the cells to form embryoid bodies. Embryoid bodies are plated directly onto a suitable substrate with or without an extracellular matrix component such as fibronectin or laminin, and cultured in a suitable differentiation nutrient medium adapted to promote differentiation into neuroprogenitor cells, such as nestin-positive neuroprogenitor cells. Nestin is a cell marker characteristic of neural precursors cells. In another embodiment, the pluripotent stem cells are first aggregated into a heterogeneous cell population by forming embryoid bodies, for example by culturing the pluripotent stem cells in suspension. These cells can be cultured in nutrient medium with or without serum, as well as with one or more of the differentiation agents listed above, to promote differentiation of cells in the embryoid bodies. Preferably the pluripotent stem cells are cultured in ES cell medium without LIF.

As used herein, the term "embryoid bodies" refer to an aggregation of differentiated cells generated when pluripotent stem cells are grown in suspension culture, or overgrow in monolayer cultures. Embryoid bodies may also have undifferentiated cells in the aggregation of cells. Preferably this aggregation of cells is surrounded by primitive endoderm. Embryoid bodies typically contain cells derived from all three germ layers, ectoderm, mesoderm and endoderm. In mature human embryoid bodies, it is possible to discern cells bearing markers of various cell types, such as neuronal cells, haematopoietic cells, liver cells, and cardiac muscle cells. Some cells in mature embryoid bodies can behave functionally like differentiated cells. For example, active cardiac muscle cells can cause an embryoid body to pulsate. Preferably the differentiation of pluripotent stem cells is controlled so that specific cell types can be obtained for therapeutic purposes.

The embryoid bodies are cultured until they reach sufficient size or desired differentiation, for example after 3-10 days of culture, preferably 4-8 days, and then plated onto a substrate. Preferably the substrate is coated with extracellular matrix components, including but not limited to poly-L-lysine, poly-L-ornithine, laminin, collagen, fibronectin, Matrigel®, or combinations thereof. The embryoid bodies are preferably plated directly onto the substrate without dispersing the cells. The embryoid bodies are then cultured under conditions to encourage further differentiation of the plated cells into neuronal or CNS precursor cells. For example, the embryoid bodies may be cultured in a serum-free defined medium that is selective for nestin-positive cells, such as ITSFn medium. Alternatively, the expanded pluripotent stem cells can be plated directly on a substrate and cultured in serum-free defined medium to select for nestin-positive cells. Nestin is an intermediate filament protein expressed in the neuroepithelium.

Preferably, the serum-free defined medium used for expansion of embryoid bodies is DMEM:F-12 supplemented with one or more growth factors selected from the group consisting of progesterone, putrescine, laminin, insulin, sodium selenite, transferrin, fibronectin, FGF, SHH, EGF, and BDNF. More preferably, the serum-free defined medium is ITSFn medium, which is supplemented with the nutrients insulin, sodium selenite, transferring, and fibronectin. Generally, the cells are grown under these conditions for a period of 5-16 days, more preferably for 7 days. In preferred embodiments, selection with the above serum-free defined medium enriches the population of viable nestin-positive cells to about 40-70%, more preferably to about 80%-90%, and most preferably to about 95%-99%.

Next, the neuronal or CNS precursor cells generated are expanded in CNS expansion media. As used herein, the terms "expand" or "expansion" refer to a process by which the number or amount of cells is increased due to cell growth and division. The term "proliferate" may be used interchangeably with "expand" or "expansion." Preferably the CNS expansion media comprises a minimal essential medium such as DMEM/F12, and is supplemented with additives that help sustain cultures of neural cells, for example N2 and B27 additives. The CNS expansion media also preferably includes one or more neural-inducing agents to encourage proliferation of CNS precursor cells and to increase the efficiency of the generation of GABAergic neurons, for example basic fibroblast growth factor (bFGF), as well as other factors that control GABAergic neuron fate during embryogenesis in vivo. Preferably, the neuronal or CNS precursor cells are grown in the CNS expansion media for 4-10 days. Additionally, the cells are preferably plated on a surface that permits adhesion of neuronal or CNS precursor cells, such as surfaces coated with poly-1-lysine, poly-L-ornithine, laminin, collagen, fibronectin, Matrigel®, or combinations thereof.

In one embodiment, the embryoid bodies are generated from murine ES cells by culturing the cells on a bacteriological plate in the absence of feeder cells in an appropriate media. Preferably, murine ES cells are first dissociated, for example by exposure to trypsin, followed by scraping and breakdown of the cells into small clusters. These clusters are then plated at an appropriate density onto bacteriological dishes that preferably have a non-adhesive surface, which prevents attachment of the cells, thereby stimulating differentiation and formation of embryoid bodies. The cells are cultured in an appropriate medium, for example ES medium, which preferably contains DMEM with high glucose or knockout DMEM supplemented with 10-20% FCS, FBS, or knockout serum replacement, as well as other supplements such as β-mercaptoethanol, L-glutamine (2 mM), and antibiotics. The medium is changed at least every other day, and the embryoid bodies are allowed to grow, preferably for about 4-8 days.

In another embodiment, the embryoid bodies are generated from human ES cells by culturing the cells on a bacteriological plate in the absence of feeder cells in an appropriate media. Preferably the human ES cells are dissociated into clusters and then plated in non-adherent plates to facilitate the development of embryoid bodies. The appropriate media preferably contains DMEM with high glucose and is supplemented with 10-20% FCS. Other supplements may also be added to the media, such as 0.1 mM 2-mercaptoethanol, 2 mM L-glutamine, 50 U/ml of penicillin, and 50 µg/ml of streptomycin.

After the embryoid bodies are isolated, the embryoid bodies are replated on a culture plate coated with 0.1% to 0.2% gelatin in serum-free medium for selection of neuroprogenitor and CNS precursor cells, preferably nestin-positive cells. Preferably the serum-free medium is a basal medium such as DMEM:F-12, which is supplemented with growth factors. ITSFn medium, which is a medium that selects for nestin-positive cells, contains the basal medium DMEM:F-12 (1:1) or IMDM medium, supplemented with the growth factors insulin, sodium selenite, transferrin, and fibronectin.

Preferably, these neuroprogenitor or CNS precursor cells, preferably nestin-positive cells, are next cultured in CNS expansion media which contain neural-inducing growth factors that select for neuronal precursors, preferably GABAergic neuronal precursors. One example of CNS expansion media contains DMEM/F12 medium supplemented with N2, B27, and bFGF. The neuroprogenitor or CNS precursor cells are also re-plated on another culture dish pre-coated with extra-cellular matrices, for example poly-L-lysine, poly-L-ornithine, laminin, collagen, or combinations thereof. Although not wishing to be bound by any particular mechanism, it is believed that these various factors present in the CNS expansion media contribute to the overall increase in the percentage of neuronal cells and further induce differentiation of the GABAergic neuron phenotype. In preferred embodiments, the nestin-positive precursor cells grown in the CNS expansion media for 5-8 days.

Differentiation of GABAergic Neurons

The neuroprogenitor cells prepared according to the methods disclosed herein can be further differentiated into high proportions of mature neurons, for example GABAergic neurons, as well as dopaminergic, serotonergic, and glutamatergic neurons. The neuroprogenitor cells can also be further differentiated into glial cells such as oligodendrocytes or astrocytes. Terminal differentiation of the neuroprogenitor or CNS precursor cells is achieved by culturing the cells according to differentiation protocols disclosed herein.

Preferably, the nestin-positive neuroprogenitor or CNS cells are expanded 2, 3, 4, 5, 6, 7, 8, 9, 10, 11, 12, 13, 14, 15, 16, 17, 18, 19, or 20 days in a differentiation media which facilitates the differentiation of the neuroprogenitor or CNS cells into terminally differentiated neural cells or mature neurons. In addition, differentiation may be facilitate by withdrawing some or all of the factors that promoted the differentiation, proliferation, or both of the neuroprogenitor or CNS cells, such as β-FGF. For example, the expanded neuroprogenitor or CNS cells may be differentiated by culturing the cells in a differentiation media containing DMEM:F-12 medium or Neurobasal A medium, supplemented with FCS, N2, B27, or a combination thereof, with or without β-FGF. The differentiation media may also contain an array of additional factors to enhance terminal differentiation or GABAergic neuron yield, for example Ara-C. In one preferred embodiment, the neuroprogenitor or CNS cells are cultured in differentiation media containing Ara-C for one or more days, and then cultured in differentiation media without Ara-C for 5, 6, 7, 8, 9, 10, 11, 12, 13, 14, 15, 16, 17, 18, 19, or 20 days. In another preferred embodiment, the neuroprogenitor or CNS cells are cultured in differentiation media that contains DMEM:F12 media supplemented with N2 and B27 for one day; next cultured in differentiation media that contains DMEM:F12 media supplemented with 5% FBS, B27, and Ara-C for two days; and finally cultured in the same differentiation media without Ara-C for 2-16 days, preferably 12 days.

Preferably, a high percentage of the neuroprogenitor cells differentiate into GABAergic neurons, for example at least about 20%, 25%, 30%, 35%, 40%, 45%, 50%, 55%, 60%, 65%, 70%, 75%, 80%, 85%, 90%, 95%, or 99% of the cells. In one preferred embodiment, the pluripotent stem cells expanded and differentiated according to the methods disclosed herein give rise to a high percentage (at least about 60%) of GABAergic neurons. In addition, the GABAergic neurons may be further purified from a population of differentiated neural cells by methods well known to those of skill in the art, such as immunolabeling and fluorescence sorting, for example solid phase adsorption, FACS, MACS, and the like. Other differentiated neural cells derived herein, for example dopaminergic, serotonergic, and glutamatergic neurons, as well as oligodendrocytes and astrocytes, may also be isolated using similar methods.

Uses for Neuroprogenitor Cells and Differentiated Neural Cells

The neuroprogenitor cells and differentiated neural cells described herein (e.g., GABAergic, dopaminergic, serotonergic, and glutamatergic neurons, as well as oligodendrocytes and astrocytes) can be utilized for various applications, such as therapeutic applications, as well as for in vitro and in vivo assessment and screening of various compounds such as small molecule drugs for their effects on these cells. These cells can also be used to prepare cDNA expression libraries to analyze the expression patterns of these cells, as well as to prepare monoclonal or polyclonal antibodies that are specific to markers for the particular cells used, using techniques that are well known to those of skill in the art. These cells can also be use therapeutically to the benefit of individuals suffering from debilitating neurodegenerative disorders and neuronal diseases.

The present disclosure provides for the use of the neuroprogenitor cells and differentiated neural cells described herein to treat or prevent various neurodegenerative disorders and neuronal diseases in which neurons or glial cells are injured or die in the central nervous system (CNS) or spinal cord. Subjects in need of such therapy will be treated by a therapeutically effective amount of such cells to restore functions in the CNS or peripheral nervous system (PNS). As used herein, a "therapeutically effective amount" of cells is an amount sufficient to arrest or ameliorate the physiological effects in a subject caused by the loss, damage, or degeneration of neural cells, such as mature neurons (e.g., GABAergic, dopaminergic, and serotonergic neurons), astrocytes, and oligodendrocytes. For example, these cells could be used therapeutically by transplanting them directly into parenchymal or intrathecal sites of the CNS, depending on the disease or condition being treated.

These cells may be used to treat acute or chronic damage to the nervous system, as well as debilitating neurodegenerative disorders and neuronal diseases, which include disorders or diseases of the nervous system, including the CNS and PNS. Neurodegenerative disorders and neuronal diseases include but are not limited to Parkinson's disease, Alzheimer's disease, Huntington's disease, Lewy body dementia, multiple sclerosis, cerebellar ataxia, progressive supranuclear palsy, spinal cord injury, amyotrophic lateral sclerosis (ALS), epilepsy, stroke, ischemia, injury or trauma to the nervous system, neurotoxic injury, and the like. Certain neurological disorders can also be treated with differentiated neural cells derived from pluripotent cells, for example disorders associated with cognition and psychology including but not limited to anxiety disorders, mood disorders, addiction, obsessive-compulsive disorders (OCD), personality disorders, attention deficit disorder (ADD), attention deficit hyperactivity disorder (ADHD), and schizophrenia.

One embodiment of the present disclosure relates to methods of treating or preventing neurodegenerative disorders or neuronal diseases characterized by the degeneration or destruction of GABAergic neurons by administration of a therapeutically effective amount of GABAergic neurons derived from pluripotent stem cells, preferably murine or human pluripotent stem cells. Preferably, a human patient suffering from a neurodegenerative disorder or neuronal disease is treated by engrafting a therapeutically effective amount of neuroprogenitor cells and differentiated neural cells of the present disclosure into the patient. When the patient suffers from cerebral ischemia or stroke, preferably the administration of a therapeutically effective amount of GABAergic neurons will produce a reduction in the amount or severity of the symptoms associated with the cerebral ischemia or stroke such as memory loss, cognitive disorders, or motor disorders.

The therapeutically effective amount of cells used will depend on the needs of the subject, the subject's age, physiological condition and health, the desired therapeutic effect, the size of the area of tissue that is to be targeted for therapy, the site of implantation, the extent of pathology (e.g., the level of neuronal degeneration), the chosen route of delivery, and the treatment strategy. For example, treatment of a disorder affecting a larger region of the brain could require a larger number of cells to achieve a therapeutic effect when compared to a smaller target region. Cells may also be administered to more than one site in a given target tissue, with multiple small grafts of low cell doses. The cells of the present disclosure may be completely dissociated before administration, such as to create a suspension of single cells, or nearly completely dissociated before administration, such as to create small aggregates of cells. The cells may be administered in a manner that allows them to graft or migrate to the intended tissue site and reconstitute or regenerate a functionally deficient area. Preferably the cells are used for autologous therapy, thereby minimizing or eliminating immune rejection problems after transplantation, e.g. histocompatibility with the intended recipient. Alternatively, the cells are used for allogenic therapy.

A suitable range of cells that can be administered to achieve a therapeutic effect can be from about 100 to about 1,000,000 neurons, preferably from about 500 to about 500,000 neurons, or from about 1000 neurons to about 100,000 neurons. The number of cells administered will depend heavily on the number that survives therapeutic administration. Therapeutic concentrations of neural cells administered to a subject may range from about 10, 100, 500, 1000, 5000, 10,000, 15,000, 20,000, 25,000, 30,000, 35,000, 40,000, 45,000, 50,000, 60,000, 70,000, 80,000, 90,000, 100,000, 150,000, 200,000, 250,000, 300,000, 350,000, 400,000, 450,000 to about 500,000 cells per microliter of a pharmaceutically acceptable carrier. Ranges of concentrations of cells in a carrier include, for example, 100-50,000 cells/µl, 1000-10,000 cells/µl, 5000-25,000 cells/µl, 15,000-45,000 cells/µl, 20,000-50,000 cells/µl, 55,000-200,000 cells/µl, 100,000-40,000 cells/µl, 150,000-50,000 cells/µl, etc. The number of cells grafted into a transplant site will also affect therapeutic efficacy.

For therapeutic applications, it is often preferable that populations of precursors or differentiated neural cells are substantially pure of any undifferentiated pluripotent stem cells. One strategy for removing pluripotent stem cells from a therapeutic preparation is to transfect the cells with a vector that has a gene which is preferentially expressed in undifferentiated cells, the expression of which selects against the pluripotent stem cells. Suitable promoters that are preferentially expressed in undifferentiated cells are the telomerase reverse transcriptase (TERT) promoter and the OCT-4 promoter. The gene expressed in the vector may for example be lytic to the cell, such as a toxin, or it may be selected against by the application of an external agent.

The ability to generate GABAergic neurons, as well as dopaminergic and serotonergic neurons, from pluripotent stem cells as disclosed herein is of great clinical relevance for therapeutically preventing or treating a variety of neurodegenerative disorders and neuronal diseases. For example, GABAergic neurons can be used to treat or prevent neurodegenerative disorders and neuronal diseases which are characterized by abnormalities in fast inhibitory synaptic transmissions, neuronal excitability, and rapid changes in mood, such as seizure threshold, anxiety, panic, and response to stress (i.e., the "fight or flight" response), as well as abnormalities in memory, mood, or pain functions. For example, GABAergic neurons can be used to treat or prevent Parkinson's disease, Alzheimer's disease, epilepsy, Lewy body dementia, multiple sclerosis, cerebellar ataxia, progressive supranuclear palsy, spinal cord injury, amyotrophic lateral sclerosis (ALS), and Huntington's disease, as well as stroke, ischemia, cerebral ischemia, injury or trauma to the nervous system, neurotoxic injury, and the like. GABAergic neurons can also be used to treat or prevent certain neurological disorders including but not limited to disorders associated with cognition and psychology such as anxiety disorders, mood disorders, addiction, obsessive-compulsive disorders (OCD), personality disorders, attention deficit disorder (ADD), attention deficit hyperactivity disorder (ADHD), and schizophrenia.

Parkinson's disease is a motor disorder caused by progressive degeneration of dopaminergic-producing cells in the substantia niga of the midbrain. The cell-based therapy of transplanting dopaminergic neurons into the substantia nigra of a patient with Parkinson's disease has been found therapeutically effective, but symptomatic relief is incomplete (Lindvall, O., 1997, Neuroreport. 8(14):iii-x). Therefore, the transplantation of dopaminergic neurons may not be sufficient to cure Parkinson's disease, and recent findings suggest that there is another brain region, namely the subthalamic nucleus (STN), involved in the neuropathology of Parkinson's disease (Bergman et al., 1998, Trends Neurosci. 21:32-38; Luo et al., 2002, Science 298:425-29). The subthalamic region of the brain contains both glutamatergic and GABAergic neurons (Nishino et al., 1988, Japn. J. Pharmacol. 48:331-339). In a patient with Parkinson's disease, neurons located in the STN degenerate along with neurons of the substantia nigra (During et al., 2001, Hum. Gene Ther. 12(12):1589-91). Therefore, glutamatergic and GABAergic neurons may also degenerate in patients with Parkinson's disease (Luo et al., 2002, Science 298(11):425-429).

Recent findings suggest that the introduction of GAD, an enzyme which is critical for the biosynthesis of GABA, into the STN of a Parkinson's model reduces the motor abnormalities associated with Parkinson's disease (Luo et al., 2002, Science 298:425-29). Therefore, GABAergic neurons may also be useful for treating Parkinson's disease, for example by administering or transplanting GABAergic neurons into the STN. The GABAergic neurons may be administered or transplanted alone, or in association or in combination with the administration or transplantation of dopaminergic neurons in the substantia nigra. The GABAergic neurons may also be used to treat Parkinson's disease in combination with drugs derived from plant, plant-based extracts, or synthetic sources that have anti-Parkinson's, anti-neurodegenerative, or neuroprotective activities.

Alzheimer's disease involves a deficit of mainly cholinergic cells in the nucleus basalis of the brain. Although cellular administration or transplantation of cholinergic cells is an effective therapy for Alzheimer's disease, it may not be enough to cure the disease because other neuronal cell types are also lost in the brain, particularly the hippocampus, of Alzheimer's patients. For example, Alzheimer's patient suffer a tremendous loss of memory function, which may be due in part to the loss of hippocampal neurons, the majority of which are GABAergic neurons (Seidl et al., 2001, Arch. Pharmacol. 363:139-145). In addition, significant loss of GABA content was found in the temporal cortex, occipital cortex, and cerebellum of Alzheimer's patients (Seidl et al., 2001). In one embodiment, GABAergic neurons derived from pluripotent stem cells as described herein are administered or transplanted into the hippocampal cortex region of the brain alone or in combination with other neurons such as cholinergic neurons or dopaminergic neurons to treat Alzheimer's patients.

There is an absolute need to improve the ability of cells to survive various neurodegenerative disorders and neuronal diseases, including but not limited to Parkinson's disease and Alzheimer's disease, as well as cerebral ischemia and stroke. Various factors influence neuronal degeneration and death. In a preferred embodiment, factors that induce neuronal degeneration and death, for example extracellular calcium, excessive release of glutamate, or release of oxygen radicals, are blocked before neuroprogenitor cells or differentiated neural cells described herein, for example GABAergic neurons, are administered or transplanted in the brain of a patient. By blocking or antagonizing these factors at the site of cell administration or transplantation, a higher percentage of cells may survive the procedure.

In other embodiments, the present disclosure relates to the co-administration of one or more neuronal survival factors with neuroprogenitor cells and differentiated neural cells of the present disclosure to treat a neurodegenerative disorder or neuronal disease. The neuronal survival factor(s) may be administered prior to, in conjunction with, in combination with, or after the administration of the desired cells. As used herein, a "neuronal survival factor" is any substance which causes neurons (either in vitro or in vivo) that are contacted with the factor to survive for a period of time greater than would occur without the presence of the factor. Neuronal survival factors that may be used in the present therapeutic embodiment include but are not limited to GABA agonists (e.g., benodiazepines, valproate, and phenobarbital), calcium antagonists, glutamate antagonists, antioxidants, tissue plasminogen activator (t-PA), Glial-derived neurotrophic factor (GDNF), nerve growth factor (NGF), ciliary neurotrophic factor (CNTF), brain derived neurotrophic factor (BDNF), neurotrophin-3 (NT-3), neurotrophin-4 (NT-4), FGF, IL-1β, TNFα, insulin-like growth factor (IGF-1, IGF-2), transforming growth factor beta (TGF-β, TGF-β1), drugs derived from plant, plant-based extracts, or synthetic sources that have anti-Parkinson's, anti-stroke, anti-cerebral ischemic, anti-neurodegenerative, or neuroprotective activities.

In one preferred embodiment, neuronal survival factors are co-administered with neuronal cells, preferably GABAergic neurons, to treat subjects suffering from cerebral ischemia or stroke. Currently, GABA agonists (e.g., benodiazepines, valproate, and phenobarbital), calcium antagonists, glutamate antagonists, antioxidants, and other neuroprotective agents or drugs are the chemical agents used to treat cerebral ischemia or stroke. While these drugs may help relieve symptoms associated with the neurological disorders of stroke or ischemia patients, they are unable to cure these disorders. Considering their critical role in stroke or ischemia patients, these agents or drugs can be used to treat the neurological disorders and diseases associated with stroke and ischemia, in combination with GABAergic neurons derived from pluripotent cells, before, during, or after therapeutic administration of the GABAergic neurons.

In another preferred embodiment, tissue plasminogen activator (t-PA) is co-administered before, during, or after the therapeutic administration of neuronal cells, preferably GABAergic neurons, to treat subjects suffering from cerebral ischemia or stroke. Recombinant forms of t-PA have been used to remove blood clots or blockage associated with cerebral ischemia or stroke in patients, and is the only FDA approved therapy for cerebral ischemia or stroke. The prognosis of a patient suffering from a stroke or cerebral ischemia is improved by supplying blood as soon as possible to the damaged site(s), preferably the hippocampus, cortex, and thalamus regions of the brain, particularly before administering neuronal cells of any type in the damaged site(s) of the brain. This may be achieved by administering t-PA to the patient, which will improve the survival of the administered neurons in the host environment by unblocking blood vessels, thereby providing sufficient oxygen and nutrients to the neurons.

As used herein, the terms "to treat", "treatment", or "therapy" refer to both therapeutic treatment and prophylactic or preventative measures. Therapeutic treatment includes but is not limited to reducing or eliminating the symptoms of a particular disease or disorder, or slowing or attenuating the progression of, or curing an existing disease or disorder. Therefore, those in need of treatment include those already diagnosed with a neurodegenerative disorder or neuronal disease, as well as those in which a neurodegenerative disorder or neuronal disease is to be prevented. The methods of the present disclosure can be used to treat any mammal in need of treatment, including but not limited to humans, primates, and domestic, farm, pet, or sports animals, such as dogs, horses, cats, sheep, pigs, cattle, rats, mice, etc. A "disorder" is any condition that would benefit from treatment with neuroprogenitor cells, differentiated neural cells, or any type of cell derived according to the methods of the present disclosure. Examples of disorders and diseases that would benefit from treatment with cells of the present disclosure, in particular GABAergic neurons, are Parkinson's disease, Alzheimer's disease, Huntington's disease, Lewy body dementia, multiple sclerosis, cerebellar ataxia, progressive supranuclear palsy, spinal cord injury, amyotrophic lateral sclerosis (ALS), epilepsy, stroke, ischemia, and the like, as well as disorders associated with cognition and psychology including but not limited to anxiety disorders, obsessive-compulsive disorders (OCD), personality disorders, attention deficit disorder (ADD), attention deficit hyperactivity disorder (ADHD), and schizophrenia.

The methods of present disclosure may be advantageously carried out by direct administration of neuroprogenitor cells or differentiated neural cells of the present disclosure to the lesioned area. Methods of neuronal transplantation and cell culture are well known to those of skill in the art, e.g., U.S. Pat. No. 5,514,552; Yurek and Sladek, 1990, Annu. Rev. Neurosci. 13:415-440; Rosenthal, 1998, Neuron 20:169-172; Vescovi et al., 1999, J. Neurotrauma 16(8):689-93; Vescovi et al., 1999, Exp. Neuro. 156(1):71-83; Brustle et al., 1999, Science 285:754-56; each specifically incorporated herein by reference. The cells may be delivered alone or in combination with other factors, for example a neuronal survival factor, and may be delivered along with a pharmaceutically acceptable vehicle. Ideally, such a vehicle would enhance the stability and delivery properties of the cells.

The present disclosure also provides for pharmaceutical compositions containing the cells which can be administered using a suitable vehicle such as liposomes, microparticles, or microcapsules. Cells of the present disclosure may also be supplied in the form of a pharmaceutical composition comprising an isotonic excipient, and prepared under conditions that are sufficiently sterile for human administration. General principles of medicinal formulations of cell compositions is found in *Cell Therapy: Stem Cell Transplantation, Gene Therapy, and Cellular Immunotherapy*, G. Morstyn & W. Sheridan eds, Cambrigge University Press, 1996, and *Hematopoietic Stem Cell Therapy*, E. Ball, J. Lister & P. Law, Churchill Livingstone, 2000, specifically incorporated herein by reference. Additionally, it may be desirable to administer a pharmaceutical composition containing a neuronal survival factor locally to the area in need of treatment, which may be achieved by, for example, local infusion during surgery, injection, a catheter means, or implant means, wherein such implant can be of a porous, non-porous, or gelatinous material, including membranes, such as silastic membranes or fibers.

The neuroprogenitor cells and differentiated neural cells of the present disclosure may be administered to a subject as either a substantially homogenous, nearly homogeneous, or heterogeneous cell population. A substantially homogenous cell population comprises greater than 75% of a single cell type, such as a GABAergic neuron, more preferably greater than 90%, and most preferably greater than 95%-99%. A heterogeneous cell population will consist of two or more cell types mixed in a single cell population, for example GABAergic neurons, dopaminergic neurons, serotonergic neurons, Schwann cells, oligodendrocytes, astrocytes, and glial cells. The cells may also be genetically altered by methods well known to those of skill in the art to express or release trophic factors, growth factors, neuronal survival factors, or other therapeutic compounds in the damaged area of the brain, central nervous system, peripheral nervous system, or other tissues. The use of promoter and cell type combinations for protein expression is generally known to those of skill in the art of molecular biology, for example, see Sambrook, et al. 1989, Molecular Cloning: A Laboratory Manual 2nd Ed. Cold Spring Harbor Laboratory Press, Cold Spring Harbor, N.Y., specifically incorporated herein by reference.

To achieve expression of trophic factors, growth factors, neuronal survival factors, or other therapeutic compounds in the neuroprogenitor cells and differentiated neural cells of the present disclosure, suitable regulatory elements can be derived from a variety of sources, and may be readily selected by one of ordinary skill in the art. Examples of regulatory elements include a transcriptional promoter, enhancer, and RNA polymerase binding sequence, as well as a ribosomal binding sequence, including a translation initiation signal. Other additional genetic elements, such as selectable markers, may also be incorporated into the recombinant molecule. The recombinant molecule may be introduced into the pluripotent stem cells, or the neuroprogenitor cells or differentiated neural cells derived from the pluripotent stem cells, using in vitro delivery vehicles or in vivo techniques. Examples of delivery techniques include retroviral vectors, adenoviral vectors, DNA virus vectors, liposomes, physical techniques such as microinjection, and transfection via electroporation or calcium phosphate precipitation, or other methods known in the art for transfer of creating recombinant cells. The genetically altered cells may be encapsulated in microspheres and implanted into or in proximity to the diseased or damaged tissue. Protocols employed are well-known to those skilled in the art, and may be found, for example, in Ausubel et al., Current Protocols in Molecular Biology, John Wiley & Sons, New York, N.Y., 1997, incorporated herein by reference.

Preferably, the cell transplant therapy of the present disclosure also incorporates some means of storing and preserving the neuroprogenitor cells and differentiated cells for use in transplant surgery, for example long-term storage by cryopreservation, or short term storage in preservation medium. Cryopreserved embryonic mesencephalic tissue has been successfully stored for up to 70 days and transplanted as homografts in rodent (Collier et al., Progress in Brain Research, Vol. 78, New York, Elsevier (1988), pp. 631-36, specifically incorporated herein by reference) and primate (Collier et al., 1987, Brain Res. 436:363-66, specifically incorporated herein by reference). It has also been demonstrated that embryonic mesencephalic cells can be successfully cultured after cryopreservation. Mesencephalic tissue can also be stored short-term (2-5 days) in preservation medium at 4° C. and subsequently transplanted with surviving graft volumes similar to those for fresh tissue (Sauer et al., 1989, Restor. Neurol. Neurosci. (Suppl.:3.sup.rd Int. Symp. Neural Tranplan.):56, specifically incorporated herein by reference). Similar techniques may be employed to store and preserve the neuroprogenitor cells and differentiated cells of the present disclosure, and such techniques are well known to those of skill in the art.

Another use for the neuroprogenitor cells and differentiated neural cells described herein is to screen for factors such as pharmaceutical compounds, solvents, small molecules, peptides, or polynucleotides, as well as for environmental factors such as culture conditions or manipulations, that affect the phenotype or characteristics of these cells. For example, biologically active molecules present in plant, plant-based extracts, or in animal, human, or synthetic sources, may be screened and evaluated using these cells. In addition, these cells can be used to assess candidate growth factors or differentiation factors. For example, a candidate pharmaceutical compound can be added to neuroprogenitor cells or mature neurons, either alone or in combination with other drugs, and any changes in the morphology, phenotype, or functional activity in the cells can be assessed and evaluated. In another embodiment, GABAergic neurons are used to screen for factors that affect receptors (e.g., agonists or antagonists) of GABAergic neuron in the CNS, PNS, or specific tissues or organs. GABAergic neurons can also be used to screen for agonists and/or antagonists of neuropeptides, neurotransmitters, neurohormones, or GABA. GABAergic neurons can also used to test the neurotoxicity of biologically active molecules.

In addition, the neuroprogenitor cells and differentiated neural cells described herein may be further modified at any stage of differentiation. For example, these cells may be genetically modified to have single or multiple genetic modifications, either transient or stable. Genetic alterations of these cells may be desirable for many reasons, such as to provide modified cells for gene therapy or replacement tissues for grafting or implantation. The cells of the present disclosure can be genetically modified through the introduction of vectors expressing a selectable marker under the control of a neural-specific promoter, which are well known to those of skill in the art. These cells may also be modified at any stage to express certain markers or genes that can be used to further purify differentiated cells derived from pluripotent stem cells, or alternatively to induce differentiation into particular cell lineages. These cells can be modified to reduce or prevent immune rejection after transplantation, i.e. histocompatibility with the intended recipient.

To increase the replicative capacity of cells generated using the present disclosure, these cells may be telomerized by genetically altering them with a suitable vector so that they express the telomerase catalytic component (TERT). The TERT sequence used may be derived from human or mouse (WO 98/14592 and WO 99/27113, specifically incorporated herein by reference), as well as other mammalian species. Alternatively, transcription of the endogenous TERT gene can be increased. Methods used to genetically modify cells are well known to those of skill in the art. These methods utilize various molecular biology techniques, many of which are generally described in Sambrook, et al. 1989, Molecular Cloning: A Laboratory Manual $2^{nd}$ Ed. Cold Spring Harbor Laboratory Press, Cold Spring Harbor, N.Y., specifically incorporated herein by reference.

In Vitro Transplantation With Adult Brain Cells

The human brain has little capacity for self-repair, and developing therapies for brain damage caused by disease or injury remains a great clinical challenge. While there has been much interest in the possibility of treating brain damage by cellular transplantation, this approach is still at an early experimental stage. One major hurdle in the transplantation of neural cells is the survivability of these cells, since experiments show that most grafted neurons degenerate after the transplantation. For example, the typical survival rate of dopaminergic cells grafted into experimental animals or subjects with Parkinson's disease has been limited to about 10% (Brundin et al., 1987, Ann. N.Y. Acad. Sci. 495:473-96; Nakao et al., 1995, Nat. Med. 1(3):226-31). Although the cause(s) of this low survival rate is unknown, it may be due to neurotoxic effects by the recipient's brain cells, or insufficient supply of nutrient and oxygen to the transplanted cells. Clearly, factors that cause neuronal death should be further investigated so that neuronal death after transplantation may be minimized.

One way to identify and study these factors is to create a brain-like environment and then test the efficacy or survivability of neuronal or neural cells, whether derived from pluripotent stem cells or isolated from other sources. One embodiment of the present disclosure creates this brain-like environment by using a technique of in vitro transplantation of isolated neuronal or neural cells with adult neural cells, preferably cells isolated from the adult hippocampus. As used herein, the term "in vitro transplantation" refers to culturing two different types of cells together in the same culture environment. In vitro transplantation can be used to determine the compatibility of two types of cells under similar environments and to study and predict factors that affect the survivability and functionality of transplanted cells. This system can be used to assess the survivability and functionality of the isolated neuronal or neural cells, particularly those derived from pluripotent cells. This assessment will in turn help determine the ability of these cells to treat neurodegenerative disorders or neuronal diseases, including but not limited to stroke, ischemia, Parkinson's disease, Alzheimer's disease, epilepsy, and Huntington's disease. In a preferred embodiment, this technique is used to assess the survivability or efficacy of GABAergic neurons derived from pluripotent cells as disclosed herein in a host-like environment. In preferred embodiments, the survivability of neuronal or neural cells, preferably GABAergic neurons, derived from pluripotent cells is at least 90% in the adult hippocampal cell environment after in vitro transplantation. In other embodiments, at least about 30%, 35%, 40%, 45%, 50%, 55%, 60%, 65%, 70%, 75%, 80%, 85%, 95%, or 99% of the GABAergic neurons survive in this environment.

The novel in vitro transplantation model disclosed herein can also be used to study the following parameters: (1) synaptic formation between and among transplanted cells and host cells; (2) factors involved in neuronal or neural death after cellular transplantation; and (3) rate of neuronal or neural death. Not only will the in vitro transplantation model help to provide detailed information required for improving cell survivability and functionality after transplantation, it will also help neurobiologists or neurosurgeons to decide on a strategy before transplanting neurons in a patient.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

The following example demonstrates the in vitro derivation of functional GABAergic neurons from murine embryonic stem cells. FIG. 1 illustrates the derivation of GABAergic neurons from murine ES cells, while FIG. 2 illustrates the different steps for differentiating murine ES cells into terminally differentiated neurons.

1) Culture and Expansion of Murine Embryonic Stem Cells:

The murine ES cells utilized in the present set of experiments were isolated from the inner cell mass of a mouse blastocyst using techniques well known to those of skill in the art. The murine ES cells were of J-1 origin (obtained from National Institute of Dental and Craniofacial Research, National Institute of Health, Bathesda, Md., USA), and were at passage 14. The cells were maintained on mitomycin-C treated mouse embryonic fibroblast feeder cells, which are mitotically inactivated in ES cell medium. The murine ES cells were cultured in the ES cell medium to expand the number of undifferentiated cells. Generally, ES cells can be expanded at least about 1000 fold without losing pluripotency. The ES medium used generally included a carbon source, a nitrogen source, and a buffer to maintain the desired pH. The ES cell medium consisted of Dulbecco's modified Eagles medium (DMEM) or knockout DMEM (Gibco), supplemented with 10-20% ES cell qualified fetal bovine serum (FBS) (Hyclone) or serum replacement knockout serum (Gibco), 1% MEM non-essential amino acid solution, 2 mM L-glutamine, and 0.1 mM β-mercaptoethanol. The ES medium was also supplemented with leukemia inhibitory factor (LIF) at a concentration of 1000 units/ml (ESGRO, Chemicon International Inc.) to inhibit differentiation of the murine ES cells.

The murine ES cells were expanded by culturing and regularly passaging the ES cells in ES cell medium to inhibit differentiation again using techniques well known to those of skill in the art. The ES cells were cultured on tissue culture plates treated with 0.1% to 0.2% gelatin in phosphate buffered saline (PBS) at 37° C. for at least 1-2 hours. The ES cells were grown on mouse feeder cells inactivated with mitomycin-C at a concentration of $1 \times 10^5$/ml. The ES cells were incubated for 4 days at a temperature between about 35° C.

and 40° C., preferably about 37° C., between about 1% and 10% $CO_2$ atmosphere, more preferably at 5% $CO_2$ atmosphere. The ES medium was changed every day or every other day depending on the growth of ES cells in culture.

2) Generation of Embryoid Bodies:

After the undifferentiated murine ES cells were proliferated and expanded, they were cultured to form embryoid bodies. First, the ES cells were dissociated by brief exposure to 0.05% trypsin-EDTA, followed by scraping and breakdown of the cells into small clusters. These clusters were then plated at a density of approximately $4\times10^5$ cells/ml onto 60 mm bacteriological dishes in the absence of feeder cells in an appropriate media. The bacteriological dishes used have a non-adhesive surface that prevents attachment, thereby stimulating differentiation of the ES cells and formation of embryoid bodies. These cells were cultured as a suspension culture in ES medium. The ES medium used to culture these cells had DMEM with high glucose or knockout DMEM which was supplemented with 10-20% FBS or knockout serum replacement, as well as other supplements such as β-mercaptoethanol (0.1 mM), L-glutamine (2 mM), and antibiotics. No bFGF or LIF was added to the ES medium. On the following day, the cell suspension was transferred to a new culture plate, leaving behind any cells attached to the previous plate. The ES cell medium was changed every other day by centrifuging the cells out of the old medium, resuspending the cells in fresh medium, and returning the cells to a non-adhesive culture plate. The embryoid bodies were allowed to grow for 4-8 days. At the end of the 4-8 days, the embryoid bodies were collected and spun down at low speed (1000 rpm, 5 minutes) and resuspended in ES cell medium. About 30-40 embryoid bodies were then transferred to an uncoated tissue culture plate and incubated for 24 hours.

3) Selection and Expansion of Nestin-Positive Neuroprogenitor Cells:

After 24 hours, nestin-positive cells (neuroprogenitor cells) were selected by replacing the ES cell medium with ITSFn (nestin selection) serum-free defined medium. The ITSFn medium consisted of DMEM:F12 medium (Gibco) supplemented with the growth factors insulin (5-25 μg/ml) (Sigma), sodium selenite (1-5 nM) (Sigma), transferrin (1-10 μg/ml) (Gibco), and fibronectin (1-5 μg/ml). Generally, the cells were incubated in the ITSFn medium for about 6-10 days, more preferably for about 7 days, with the ITSFn medium being replenished every other day. The cells were generally grown at about 35° C. and 40° C., preferably about 37° C., and between about 1% and 10% $CO_2$ atmosphere, more preferably between about 2% and 6% $CO_2$ atmosphere. After complete selection, preferably for 7 days, the neuroprogenitor cells were characterized for nestin expression using an immunofluorescence technique, which showed that approximately 90% of the cells were positive for nestin expression. The nestin-positive cells were subsequently expanded as described below.

The nestin-positive cells were dissociated using 0.05% trypsin-EDTA and plated onto poly-L-orinithin/laminin coated plated containing CNS expansion media. The CNS expansion media contained DMEM:F12 supplement with N2 (10 ug/ml) and B27 (20 ug/ml). A nerve growth factor was also added to the CNS expansion media, βD-FGF (10-20 ng/ml), which is known to enhance the neuronal productivity. The neuronal precursor cells were expanded for 6 days, to generate a large number of neuronal cells. The cells were grown in the CNS expansion media for 6 days, with the media being replenished every two days.

Figure 6:
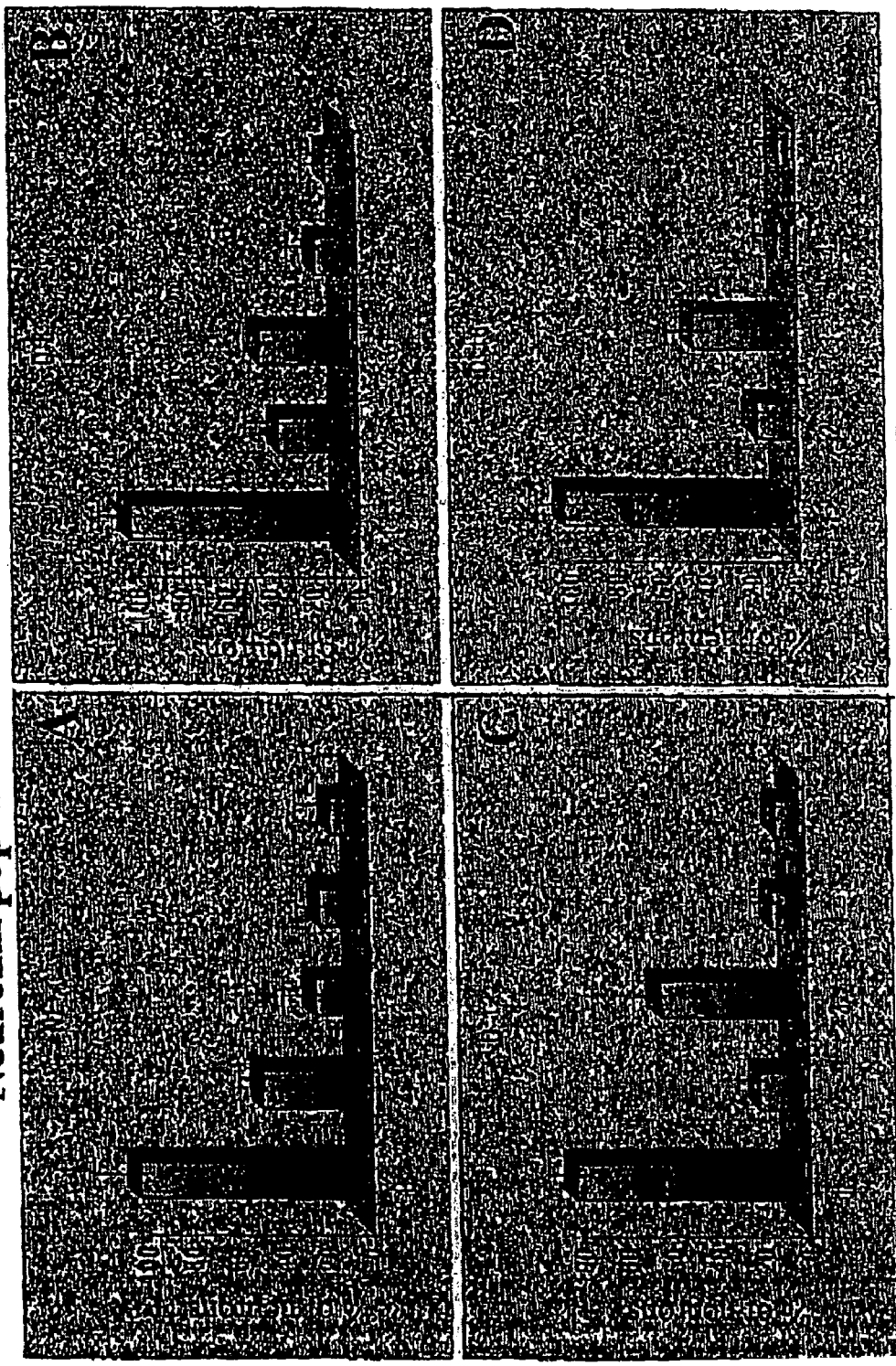
FIG. 6 is a comparative analysis of neuronal populations derived from murine ES cells. The total numbers of cells at different stages of derivation were counted using morphometrical analysis. The stages of derivation analyzed were expansion of (a) nestin-positive cells (NE); (b) 8 days of differentiation; (c) 12 days of differentiation; and (d) 16 days of differentiation. The cells were quantified according to: (1) total neurons; (2) glutamate expression; (3) GABA expression; (4) tyrosine hydroxylase (TH) expression; and (5) HT expression.

4) Differentiation of Neuronal Progenitor Cells:

The expanded neuronal progenitor cells were differentiated by culturing the cells in a differentiation media containing Neurobasal A medium (Gibco), FCS (10-20%) (HY-CLONE), and B27 supplement (2-10%) (Gibco), but no β-FGF. Additionally, the differentiation media contained factors to enhance GABAergic neuron yield, preferably Ara-C (Sigma Chemical Co. USA). Culturing the neuronal progenitor cells in differentiation media containing Ara-C (20 ug/ml) increased the percentage of GABAergic neurons in the neuronal population derived from murine ES cells. After 3 days of culture in the differentiation media containing Ara-C, the cells were grown in the same media without Ara-C for 8, 12, or 16 days. When the neuronal progenitor cells were cultured in differentiation media containing Ara-C for 3 days, and the cells were then grown in differentiation media without Ara-C for 16 days, at least about 60% of the neuronal progenitor cells differentiated into GABAergic neurons (FIG. 6).

5) Characterization of Differentiated Neurons

An analysis of the total population of neuronal cells generated using the above methods demonstrated that more than 90% of the differentiated cells were neuronal cells. The differentiated neuronal cell types generated according to the present disclosure were evaluated both by the overall morphology of the cells, as well as the phenotypes identified by immunoflourescence. Immunoflourescence analysis was carried out at the neuroprogenitor expansion stage, as well as after 4, 8, 12, and 16 days of differentiation as disclosed in the protocol above. First, the isolated cells were grown in 2-well chamber slides, rinsed with PBS, and fixed for 10 minutes with 4% paraformaldehyde at room temperature. Next, the cells were permeabilized with 0.2% Triton X-100 in PBS containing 1% normal goat serum, and then blocked with 1% bovine serum albumin (BSA)/PBS for 1 hour at room temperature.

The cells were then incubated overnight at 4° C. with a primary antibody (antibody dilution was made in 1% BSA). The following primary antibodies were employed in the immunoflourescence investigation: Monoclonal GABA, 1:200 (Chemicon Inc. USA); Polyclonal GABA, 1:500 (Chemicon Inc. USA); GAD65, 1:500 (Chemicon Inc. USA); GAD67, 1:500 (Chemicon Inc. USA); GAT-1, 1:500 (Chemicon Inc. USA), GAT-2, 1:500 (Chemicon Inc. USA); Glutamate, 1:500 (Chemicon Inc. USA); Nestin, 1:50 (Chemicon Inc. USA); Oligodendrocytes, 1:500 (Chemicon Inc. USA); Serotonin, 1:500 (Chemicon Inc. USA); Tyrosine hydroxylase, 1:800 (Chemicon Inc. USA); MAP-2, 1:500 (Chemicon Inc. USA); and GFAP, 1:500 (Chemicon Inc. USA). After overnight incubation with the primary antibody, the cells were washed with PBS and incubated with an FITC labeled secondary antibody for one hour in a dark environment. The cells were then washed three times with PBS and covered with mounting media. The chamber slides were observed under fluorescence microscope to evaluate the immunopositive cells in the different stages of differentiation.

Immunofluorescence analysis of the differentiated cultures revealed that about 90% of the differentiated neuronal cells were immunoreactive to neuron-specific markers, such as Gad-65, Gad-67, GAT-1, GAT-2, Glutamate, GABA, Nestin and MAP-2 (FIG. 3). Of the total neuronal cells in the culture, about 60% of the neuronal cells stained for GABA, the marker for GABAergic neurons, while about 15% of the neuronal cells stained for tyrosine hydroxylase (TH), the marker for dopaminergic neurons. In addition, about 10% of the neuronal cells stained for glutamate, while about 5% of the neuronal cells stained for serotonin, the marker for serotonergic neurons. Finally, about 5-10% of the cells stained as oligodendrocytes. The cell culture also included glial cells, typically between about 5% to 10% of the cell population. Analysis demonstrated that at least some of the differentiated neurons in the cell culture were synaptically active. Typically, mature neurons are identified by the presence of long axonal projections with lots of fine spine-like structures. The presence of myelin-associated protein-2 (MAP-2) in the axonal projections also indicates maturation of neurons.

The differentiated cells were also analyzed by double-labeling the cells with primary antibodies to determine whether the expression of GAD65 and GAD67 was colocalized (FIG. 4). GAD65 and GAD67 are two genes expressed in GABAergic neurons that are required for the synthesis of GABA. The differentiated neuronal cell population was studied by employing a double-immunolabeling technique using GAD65/GAD67 and GABA antibodies, as described above. The double-immunolabeling results suggested that neuronal cells that express GAD65 and GAD67 proteins also express GABA neurotransmitters (FIG. 4). These results confirm that GABAergic neurons derived using the disclosed methods are GABA-producing cells. The neuronal cells that expressed GAD65 and GAD67 protein were also shown to express GABA during early development because glutamate was converted in GABAergic neurons in the presence of GAD65 and GAD67 enzymes.

The gene expression profiles of cells collected at different stages of differentiation were also analyzed. Cells were collected for analysis by Reverse Transcriptase Polymerase Chain Reaction (RT-PCR) from each of the following stages of the disclosed method: (1) Undifferentiated; (2) Embryoid Bodies (EBS); (3) Nestin Expansion; (4) 2 days of differentiation; (5) 4 days of differentiation; (6) 8 days of differentiation; (7) 12 days of differentiation; and (8) 16 days of differentiation. After the cells were collected they were pelleted, and total cellular RNA was extracted from the cell pellets using the RNeasy Qiagen kit. The isolated RNA was stored at −20° C. The total cellular RNA was treated with RNase-free RQ DNase (Promega Corp., Madison, Wis.) to remove all traces of DNA. cDNA was synthesized from the isolated total RNA using Moloney Leukemia virus superscript II reverse transcriptase following the manufacturer's instructions Random hexamer primers (GIBCO/BRL) were used to prime the reverse transcriptase (RT) reactions.

The cDNA synthesized by this reverse transcriptase reaction was used for PCR amplification with different sets of specific primers to determine which genes were expressed in the collected cells. The primers were designed to identify mRNAs expressed in GABAergic neurons, specifically the glutamate decarboxylase genes (GAD1 and GAD2), the alternatively spliced GAD1 embryonic RNA, and the vesical inhibitory amino acid transporter (VIAAT) transcript. GAD 1 is alternatively spliced during development, and the embryonic transcript is predominantly expressed in neural stem/progenitor cells during fetal development. The expression of a ubiquitously expressed gene, β-Actin, was also monitored as a positive control. These PCR reactions were carried out using only 10% of the total first strand reaction (cDNA synthesized by RT) as the template and platinum Taq polymerase under standard PCR conditions, which are well known to those of skill in the art. The general cycling parameters used to amplify DNA products were as follows:

1. denaturation of the template cDNA at 94° C. for 30 seconds;
2. annealing the primers at 55-65° C. for 1 minute, depending on the primers used; and
3. incubating the reaction at 72° C. for 1 minute, and repeating steps 1-3 (cycles) between 25 and 40 times.

After the PCR reaction, the products were run through an agarose gel using electrophoresis along with a DNA size ladder. The expression of GAD1, GAD2, GAD1 embryonic, VIAAT, and β-Actin were all analyzed by RT-PCR using the primers as set forth in Table 1:

TABLE 1

Primer sets used to amplify GABAergic neuron specific genes

| Gene | Primer Sequence |
| --- | --- |
| GAD1 (302 bp) | Sense: CCT TCG CCT GCA ACC TCC TCG AAC (SEQ ID NO: 1) <br> Anti-sense: GCG CAG TTT GCT CCC CGT TCT T (SEQ ID NO: 2) |
| GAD2 (583 bp) | Sense: ACT CTG GCA TTT CTA CAA GAT GTT AGT A (SEQ ID NO: 3) <br> Anti-sense: GAA TCA CAC TGT CTG TTC CAA TCC CTA A (SEQ ID NO: 4) |
| GAD1 embryonic (234 bp GAD1; 320 bp GAD1 embryonic) | Sense: TGG TTG ACT GTA GAG ACA CCC TGA ADT A (SEQ ID NO: 5) <br> Anti-sense: TCC CAT CAC CTT TAT TTG ACC ATC C (SEQ ID NO: 6) |
| VIATT (572 bp) | Sense: TCC TGT CCT TTT CTC CCG CCC CGC C (SEQ ID NO: 7) <br> Anti-sense: GCA CCA CCT CCC CGT CTT CGT TCT CCT C (SEQ ID NO: 8) |
| β-Actin (220 bp) | Sense: GGG TCA GAA GGA CTC CTA TG (SEQ ID NO: 9) <br> Anti-sense: GTA ACA ATG CCA CCA TGT TCA AT (SEQ ID NO: 10) |

Figure 5:
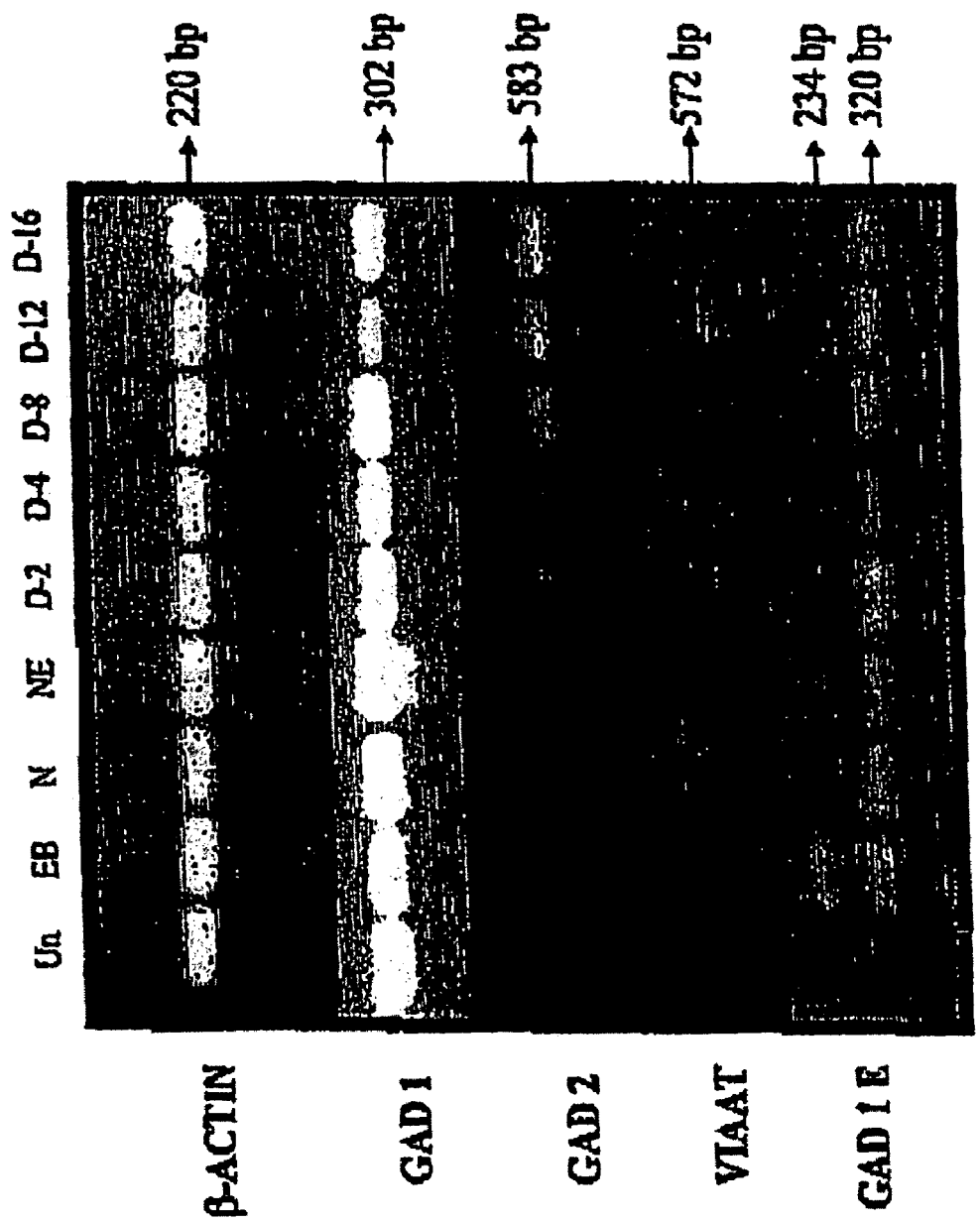
FIG. 5 shows the gene expression profile of GABAergic-neuron-specific factors in murine ES cells, and at various stages during the in vitro differentiation of these cells into GABAergic neurons. These stages were undifferentiated murine ES cells (Un), embryoid bodies (EB), nestin-selection (N), nestin-expansion (NE), 2 days of differentiation (D-2); 4 days of differentiation (D-4); 8 days of differentiation (D-8); 12 days of differentiation (D-12); and 16 days of differentiation (D-16). The expression of the following GABAergic neuron specific genes were analyzed: GAD 1, GAD2, VIAAT, and GAD 1 embryonic transcripts. GAD1 expression was observed in all stages, including in the undifferentiated ES cells. GAD2 expression was observed in the nestin-selection, nestin-expansion, and all differentiated stages, but no expression was present in the undifferentiated and embryoid bodies stages. VIAAT expression was observed only in the differential stages, particularly day 8 and day 12 of differentiation. Interestingly, VIAAT was not expressed after 16 days of differentiation. The expression of the GAD1 embryonic gene was observed in all stages except in the undifferentiated stage. β-actin, a housekeeping gene, was detected in all stages as a positive control.

The above analysis by RT-PCR demonstrated that many ES cell-derived neuronal cells spontaneously differentiated into neurons that expressed markers of the GABAergic phenotype. A difference was found in the expression of GAD1 and GAD2 throughout the different stages of cell culture analyzed. The GAD1 gene was expressed in almost all the stages (stage 1 to stage 5), including in the undifferentiated stage (FIG. 5). This is consistent with a previous report of GAD1 expression in ES cells (Bain et al., 1993, Brain Res. Mol. Brain Res. 17:23-30). GAD2, on the other hand, was only expressed in the differentiated stage as shown in FIG. 5. This result suggests that the GABAergic neurons generated using the disclosed methods have unequal phenotypic expression of both the GAD1 and GAD2 genes. The GAD1 embryonic spliced variant is expressed in all stages except the undifferentiated stage, while the neurotransmitters gene (VIAAT), which is known to transport GABA, is only expressed in the differentiated stages (FIG. 5). Expression of the housekeeping gene β-actin was used as a positive control (FIG. 5).

Reverse Phase High Performance Liquid Chromatography (RP-HPLC) was also used to analyze the expression of GABA by GABAergic neurons derived using the disclosed methods. Since a definitive characteristic of GABAergic neurons is the production of GABA, the functional capacity of ES cell-derived GABAergic neurons to produce GABA was evaluated by directly measuring the intracellular GABA levels using RP-HPLC. The concentration of GABA detected in each sample was determined by comparison with a standard solution of GABA injected into the column immediately before and after each experiment.

Figure 7:
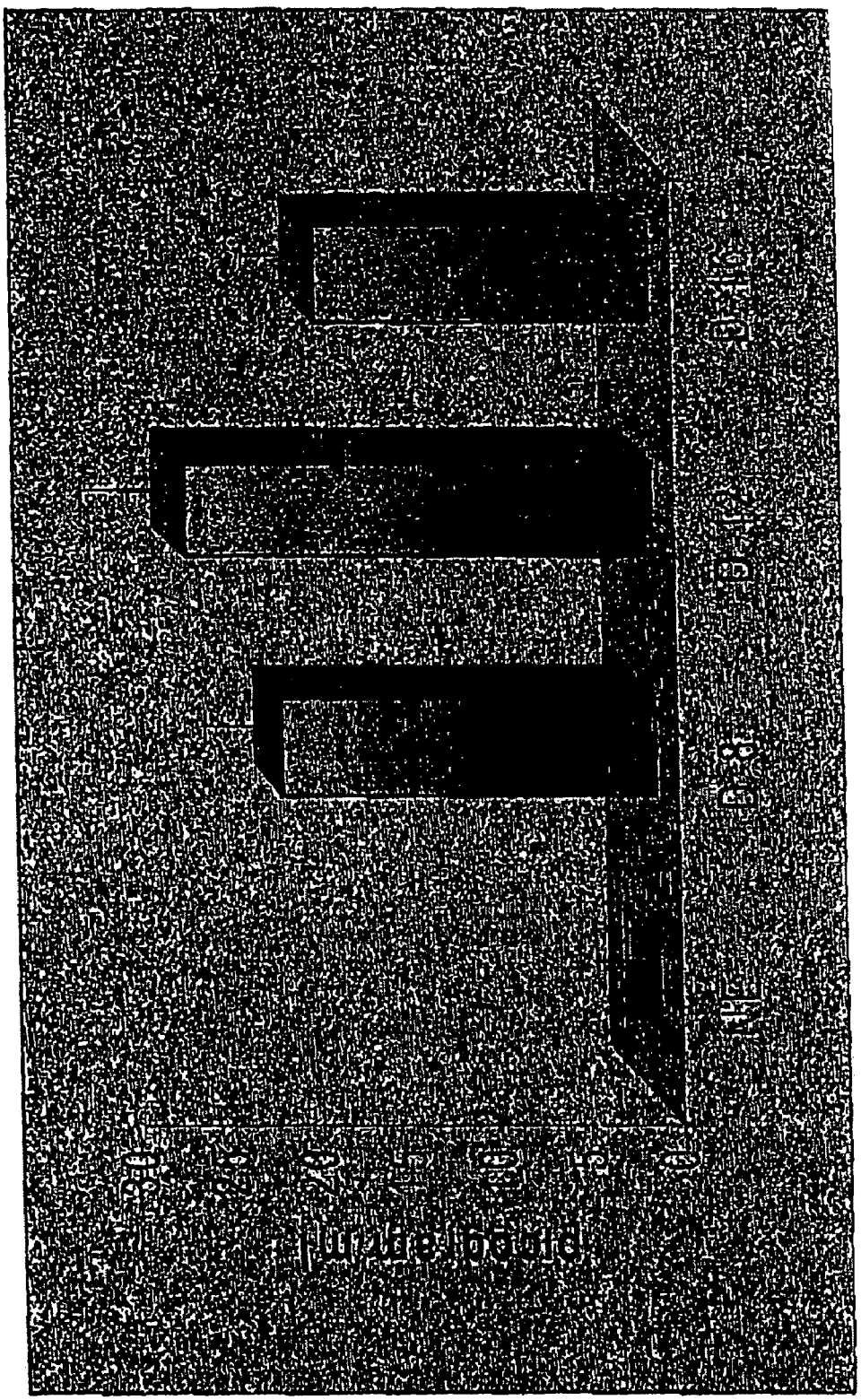
FIG. 7 shows extracellular GABA levels as determined by Reverse Phase High Performance Liquid Chromatography (RP-HPLC) in the following stages: nestin-expansion (NE); 8 days of differentiation (D-8); 12 days of differentiation (D-12); and 16 days of differentiation (D-16). GABA was only detected in the differentiated stages, and confirms that the neurons derived from murine ES cells using the methods disclosed herein produce GABA.

To begin, cells were collected at different stages of the disclosed method: Nestin-expansion stage and differentiated cells isolated after 8, 12, and 16 days of differentiation. The culture supernatants were collected from the different stages, immediately treated with 7.5% orthophosphoric acid and metabisulphite (0.22 mg/ml) to stabilize the neurotransmitter for measurement, and stored at −80° C. until analysis by RP-HPLC. Intracellular levels of GABA were detected using isocratic HPLC method based on the electrochemical detection of GABA derivation with OPA/t-butylthiol (Kehr and Ungerstedt, 1988, J. Neurochem. 51(4):1308-10; Osborne et al., 1991, J. Neurosci. Method 34: 99-106, both specifically incorporated herein by reference). The HPLC data were normalized against GABA standards at varying flow rates and sensitivities (FIG. 7).

While no GABA was detected in the nestin or nestin expansion stages, the measured levels of GABA for day-8 of differentiation was 20.95 pg/ml, while day-12 and day-16 of differentiation measured 26.18 pg/ml and 18.60 pg/ml respectively. This analysis demonstrated that the highest levels of GABA were produced by the GABAergic neurons derived above on day-12 of differentiation. The overall release of GABA from the cultured cells was 21.51 pg/ml.

Since the highest levels of GABA were produced by GABAergic neurons derived on day-12 of differentiation, cells at this same stage of differentiation were evaluated for the presence of GABA-A and GABA-B receptors. The distribution of functional neurotransmitter receptors, for example GABA-A and GABA-B receptors, on the surface of neurons, for example GABAergic neurons, is highly relevant to synaptic transmission and signal processing (Eder et al., 2001, Eur. J. Neurosci. 13:1065-69). It is known that both GABA-A and GABA-B receptors on mature GABAergic neurons are critical for normal functioning of these neurons.

To determine whether the GABAergic neurons derived from murine ES cells as described herein also express these GABAergic receptors, the cells were immunostained using anti-GABA-A receptor antibody, 1:250 (Chemicon, USA) and anti-GABA-B receptor antibody, 1:250 (Chemicon, USA) using the immunofluorescence protocol previously described.

Immunofluorescence analysis of day-12 differentiated cultures demonstrated that both GABA-A and GABA-B receptors are localized to differentiated GABAergic neurons. Interestingly, approximately 80% of the differentiated cells expressed the GABA-A receptor (FIG. 8), while only approximately 25% of the differentiated cells expressed the GABA-B receptor (FIG. 9). Since expression of both GABA-A and GABA-B receptors are highly relevant for synaptic transmission and signal processing, isolating GABAergic neurons that express both receptors could be critical for improsing cell functionality after cellular transplantation.

EXAMPLE 2

The following example, applicants of the present disclosure use an in vitro transplantation model to study the efficacy, survivability, and functionality of GABAergic neurons derived from murine embryonic stem cells. FIG. 1 illustrates the in vitro transplantation model.

The survivability and functionality of the GABAergic neurons derived from murine ES cells was studied by in vitro transplantation of the GABAergic neurons with hippocampal cells of the adult mouse brain. The hippocampal cells were isolated by first isolating cells from the hippocampus of the adult mouse brain, disassociating these cells with 0.05% trypsin-EDTA, and culturing the cells for one week in Neurobasal-A media supplemented with B27 (20 μg/ml) and N2 (10 μg/ml). The adult hippocampal brain cells were grown on 100 mm tissue culture plates coated with poly-L-ornithine and laminin or gelatin. After one week, GABAergic neurons derived from murine ES cells and collected after 12 days of differentiation were plated on the adult hippocampal brain cells, and both cell types were cultured together for one week. Approximately 90% of the GABAergic neurons survived after one week of in vitro transplantation with adult hippocampal brain cells. This result suggests that neurons derived from pluripotent stem cells are functional in the adult brain environment and make synaptic connections with adult brain cells, which also suggests that these cells may be used therapeutically to treat a variety of neurodegenerative disorders or neuronal diseases.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the methods described herein without departing from the concept, spirit and scope of the invention. More specifically, it will be apparent that certain agents that are chemically or physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A method of generating a differentiated neural cell population from mammalian pluripotent stem cells comprising the following steps:
   (a) expanding a culture of pluripotent stem cells;
   (b) culturing the pluripotent stem cells to select for neuroprogenitor cells that are positive for nestin;
   (c) isolating the nestin-positive cells;
   (d) expanding the nestin-positive neuroprogenitor cells; and
   (e) differentiating the nestin-positive cells to generate a differentiated cell population by culturing the cells in a differentiation media which comprises cytosine β-d-Arabino furanoside (Ara-C).

2. The cell population of claim 1, wherein the mammalian pluripotent stem cells are murine embryonic stem cells.

3. The cell population of claim 1, wherein the mammalian pluripotent stem cells are human embryonic stem cells.

4. The method of claim 1, wherein the differentiated cell population comprises at least about 60% GABAergic neurons.

5. The method of claim 1, wherein the differentiated cell population comprises at least about 15% dopaminergic neurons.

6. The method of claim 1, wherein the differentiated cell population comprises at least about 10% glutamatergic neurons.

7. The method of claim 1, wherein the differentiated cell population comprises at least about 5% serotonergic neurons.

8. The method of claim 1, wherein the differentiated cell population comprises at least about 5% oligodendrocytes.

9. The method of claim 1, wherein the differentiated cell population comprises at least about 5% astrocytes.

10. The method of claim 1, wherein the neuroprogenitor cells that are positive for nestin are selected by culturing the stem cells in serum-free medium.

11. The method of claim 10, wherein the serum-free medium is ITSFn serum-free defined medium.

12. The method of claim 11, wherein the cells are grown in the ITSFn serum-free defined medium for 6-10 days.

13. The method of claim 10, wherein the serum-free medium comprises one or more soluble factors selected from the group consisting of insulin, sodium selenite, transferrin, and fibronectin.

14. The method of claim 1, further comprising culturing the mammalian pluripotent stem cells of step (b) to form embryoid bodies.

15. The method of claim 14, wherein the embryoid bodies are cultured to select for neuroprogenitor cells that are positive for nestin.

16. The method of claim 15, wherein the neuroprogenitor cells comprise at least about 90% nestin-positive cells.

17. The method of claim 14, wherein the neuroprogenitor cells that are positive for nestin are selected by culturing the embryoid bodies in serum-free medium.

18. The method of claim 17, wherein the serum-free medium is ITSFn serum-free defined medium.

19. The method of claim 17, wherein the serum-free medium comprises one or more soluble factors selected from the group consisting of insulin, sodium selenite, basic fibroblast growth factor, transferrin, and fibronectin.

20. The method of claim 1, further comprising expanding the nestin-positive neuroprogenitor cells of step (c) in CNS expansion media.

21. The method of claim 20, wherein the nestin-positive neuroprogenitor cells are plated on a culture dish pre-coated with poly-L-ornithine or laminin.

22. The method of claim 20, wherein the CNS expansion media comprises one or more soluble factors selected from the group consisting of N2 supplement, B27 supplement, and a neural-inducing agent.

23. The method of claim 22, wherein the neural-inducing agent is basic fibroblast growth factor (bFGF).

24. The method of claim 20, wherein the cells are grown in the CNS expansion media for 6-10 days.

25. The method of claim 1, wherein the differentiation media comprises N2 supplement, B27 supplement, or both, but not basic fibroblast growth factor (bFGF).

26. The method of claim 1, wherein the cells are grown in the differentiation media for 2 or more days.

27. The method of claim 1, further comprising step (e), wherein the differentiated cell population of step (d) are further differentiated by culturing the cells in a second differentiation media that does not contain cytosine β-d-Arabino furanoside (Ara-C).

28. The method of claim 27, wherein the differentiated cell population is grown in the second differentiation media for 8-16 days.

29. A method of generating GABAergic neurons from mammalian neuroprogenitor cells, comprising enriching the neuroprogenitor cells for cells that are positive for nestin, isolating the nestin-positive cells, and differentiating the nestin-positive cells to generate GABAergic neurons by culturing the cells in the presence of cytosine β-d-Arabino furanoside (Ara-C).

* * * * *

SEQUENCE LISTING

```
<160> NUMBER OF SEQ ID NOS: 10

<210> SEQ ID NO 1
<211> LENGTH: 24
<212> TYPE: DNA
<213> ORGANISM: Mus musculus

<400> SEQUENCE: 1
ccttcgcctg caacctcctc gaac                                              24

<210> SEQ ID NO 2
<211> LENGTH: 22
<212> TYPE: DNA
<213> ORGANISM: Mus musculus

<400> SEQUENCE: 2
gcgcagtttg ctccccgttc tt                                                22

<210> SEQ ID NO 3
<211> LENGTH: 28
<212> TYPE: DNA
<213> ORGANISM: Mus musculus

<400> SEQUENCE: 3
actctggcat ttctacaaga tgttagta                                          28

<210> SEQ ID NO 4
<211> LENGTH: 28
<212> TYPE: DNA
<213> ORGANISM: Mus musculus

<400> SEQUENCE: 4
gaatcacact gtctgttcca atccctaa                                          28

<210> SEQ ID NO 5
<211> LENGTH: 28
<212> TYPE: DNA
<213> ORGANISM: Mus musculus

<400> SEQUENCE: 5
tggttgactg tagagacacc ctgaagta                                          28

<210> SEQ ID NO 6
<211> LENGTH: 25
<212> TYPE: DNA
<213> ORGANISM: Mus musculus

<400> SEQUENCE: 6
tcccatcacc tttatttgac catcc                                             25

<210> SEQ ID NO 7
<211> LENGTH: 28
<212> TYPE: DNA
<213> ORGANISM: Mus musculus

<400> SEQUENCE: 7
tcctgtcctt ttctcccgcc ccgccgcc                                          28

<210> SEQ ID NO 8
<211> LENGTH: 28
<212> TYPE: DNA
```

```
<400> SEQUENCE: 8
gcaccacctc cccgtcttcg ttctcctc                                      28

<210> SEQ ID NO 9
<211> LENGTH: 20
<212> TYPE: DNA
<213> ORGANISM: Mus musculus

<400> SEQUENCE: 9
gggtcagaag gactcctatg                                               20

<210> SEQ ID NO 10
<211> LENGTH: 23
<212> TYPE: DNA
<213> ORGANISM: Mus musculus

<400> SEQUENCE: 10
gtaacaatgc caccatgttc aat                                           23
```